(12) United States Patent
Armitage et al.

(10) Patent No.: US 9,187,482 B2
(45) Date of Patent: Nov. 17, 2015

(54) HYDROCHLORIDE SALT OF((1S,2S,4R)-4-{4-[(1S)-2,3-DIHYDRO-1H-INDEN-1-YLAMINO]-7H-PYRROLO[2,3-D]PYRIMIDIN-7-YL}-2-HYDROXYCYCLOPENTYL)METHYL SULFAMATE

(75) Inventors: Ian G. Armitage, Stoneham, MA (US); Reenu Chopra, Milton Road (GB); Martin Ian Cooper, Foxton (GB); Marianne Langston, North Andover, MA (US); Steven P. Langston, North Andover, MA (US); Stepan Vyskocil, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 464 days.

(21) Appl. No.: 12/779,331

(22) Filed: May 13, 2010

(65) Prior Publication Data

US 2011/0021544 A1    Jan. 27, 2011

Related U.S. Application Data

(60) Provisional application No. 61/216,221, filed on May 14, 2009.

(51) Int. Cl.
    *C07D 487/04*      (2006.01)
    *A61K 31/519*     (2006.01)
    *A61P 35/00*      (2006.01)

(52) U.S. Cl.
    CPC ................... *C07D 487/04* (2013.01)

(58) Field of Classification Search
    CPC ............................ C07D 487/04; A61K 31/519
    USPC ........................................ 544/280; 514/265.1
    See application file for complete search history.

(56) References Cited

U.S. PATENT DOCUMENTS

| | | | |
|---|---|---|---|
| 3,622,561 | A | 11/1971 | Robins et al. |
| 4,252,951 | A * | 2/1981 | Jackson et al. ............... 540/220 |
| 5,039,689 | A | 8/1991 | Daluge |
| 5,726,302 | A | 3/1998 | Ugarkar et al. |
| 5,763,596 | A | 6/1998 | Boyer et al. |
| 5,767,097 | A | 6/1998 | Tam |
| 5,824,657 | A | 10/1998 | Hill et al. |
| 5,864,033 | A | 1/1999 | Browne et al. |
| 5,973,161 | A | 10/1999 | Crimmins |
| 6,210,917 | B1 | 4/2001 | Carson et al. |
| 6,734,283 | B1 | 5/2004 | Chau |
| 2006/0189636 | A1 | 8/2006 | Critchley et al. |
| 2007/0191293 | A1 | 8/2007 | Langston et al. |
| 2011/0136834 | A1 | 6/2011 | Critchley et al. |

FOREIGN PATENT DOCUMENTS

| | | |
|---|---|---|
| EP | 0345076 | 12/1989 |
| EP | 0832091 | 1/2004 |
| EP | 0832092 | 11/2004 |
| GB | 2284811 | 6/1995 |
| GB | 2287464 | 9/1995 |
| JP | 62-108897 | 7/1987 |
| JP | 11-228422 | 8/1999 |
| JP | 11-228446 | 8/1999 |
| WO | WO 02/32920 | 4/2002 |
| WO | WO 03/049739 | 6/2003 |
| WO | WO 03/106477 | 12/2003 |
| WO | WO 2005/007621 | 1/2005 |
| WO | WO 2005/037845 | 4/2005 |
| WO | WO 2005/039486 | 5/2005 |
| WO | WO 2005/095357 | 10/2005 |
| WO | WO 2006/002284 | 1/2006 |
| WO | WO 2006/084281 | 8/2006 |
| WO | WO 2006/084281 A1 | 8/2006 |
| WO | WO 2007/092213 A2 | 8/2007 |
| WO | WO 2008/019124 | 2/2008 |

OTHER PUBLICATIONS

Dean, J. A., Analytical Chemistry Handbook, 1995, pp. 10.24-10.26.*
West, Anthony R., "Solid State Chemistry and its Applications", Wiley, New York, 1988, pp. 358 & 365.*
Braga et al. (ChemComm., 2005, pp. 3635-3645).*
Netterwald, "Screened Gems" Drug Discovery & Development, vol. 9(9), pp. 22-26 (2007).*

(Continued)

*Primary Examiner* — Susanna Moore
(74) *Attorney, Agent, or Firm* — Finnegan, Henderson Farabow, Garrett & Dunner, LLP

(57) ABSTRACT

Disclosed is a compound of formula (I):

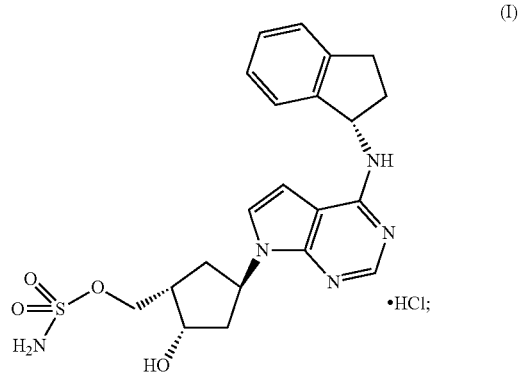

crystalline forms thereof, and solvates thereof; pharmaceutical compositions comprising a pharmaceutically effective amount of the compound of formula (I), or a crystalline form thereof, or a solvate thereof, and a pharmaceutically acceptable carrier or diluent; and the use of a compound of formula (I), or a crystalline form thereof, or a solvate thereof, for treating a patient suffering from, or subject to, a pathological condition capable of being ameliorated by inhibiting an E1 activating enzyme, particularly NAE, including, e.g., cancer.

29 Claims, 15 Drawing Sheets

(56) References Cited

OTHER PUBLICATIONS

Soucy et al. (Nature, 2009, 458, pp. 732-736).*
Soucy et al. (Nature, 2009, 458, supplemental, pp. 1-22).*
Berge (J. of Pharmaceutical Sciences, 1977, vol. 66(1), pp. 1-19).*
Bhattacharya et al. (Brittain, ed. Polymorphism in Pharmaceutical Solids, 2009, p. 334.*
International Search Report and Written Opinion of the International Searching Authority dated Aug. 26, 2010 issued in International Application No. PCT/US2010/001415.
Soucy, T.A. et al., "An Inhibitor of NEDD8-Activating Enzyme as a New Approach to Treat Cancer" *Nature* (2009), vol. 458, pp. 732-737, Supplementary Information, pp. 1-22.
Abouabdellah, Ahmed, et al., "Lewis acid-induced ene-cyclization of co-olefinic trifluoromethyl ketones: access to alicyclic compounds bearing a CF3 group," *Journal of the Chemical Society, Perkin Transactions 1: Organic and Bio-Organic Chemistry (1972-1999)*, vol. 6 (1991) pp. 1397-1403.
Baker, David C., et al., "An evaluation of certain chain-extended analogues of 9-βD-arabinofuranosyladenine for antiviral and cardiovascular activity," *Journal of Medicinal Chemistry*, vol. 26, No. 10 (1983) pp. 1530-1534.
Bernier, Stephane, et al., "Glutamylsulfamoyladenosine and pyroglutamylsulfamoyladenosine are competitive inhibitors of *E. coli* glutamyl-tRNA synthetase," *Journal of Enzyme Inhibition and Medicinal Chemistry*, vol. 20, No. 1 (Feb. 2005) pp. 61-67.
Berranger, Thierry, et al., "[2+3]-cycloadditions of enantiomerically pure oxazoline-N-oxides: a short stereoselective synthesis of (+)-carbovir," *Tetrahedron Letters*, vol. 36, No. 31 (1995) pp. 5523-5526.
Biggadike, Keith, et al., "4'-modification of carbocyclic nucleosides: synthesis of 4'-α-fluoro, 4'-α-hydroxy and 4',6'-unsaturated derivatives of the antiviral agent 2'-*ara*-fluoro carbocyclic guanosine," *Journal of the Chemical Society, Chemical Communications*, vol. 19 (1990) pp. 1380-1382.
Birman, V.B., Danishefsky, S.J. (2002) The Total Synthesis of (±)-Merrilactone A. Journal of the American Chemical Society, vol. 124, No. 10, p. 2079-2080.
Bloch, A., et al., "Inhibition of protein synthesis by 5'-sulfamoyladenosine," *Biochemistry*, vol. 10, No. 24 (1971) pp. 4394-4398.
Bookser, Brett C., et al., "Adenosine kinase inhibitors. 4. 6,8-disubstituted purine nucleoside derivatives. Synthesis, conformation, and enzyme inhibition," *Journal of Medicinal Chemistry*, vol. 48, No. 9 (2005) pp. 3389-3399.
Borthwick, Alan, et al., "Chiral carbocyclic nucleosides: the synthesis and antiviral activity of 4'—hydroxy and 4'-fluorocarbocyclic-2'-deoxyguanosines," *Bioorganic & Medicinal Chemistry Letters*, vol. 3, No. 12 (1993) 2577-2580.
Boyer, Serge H., et al., "Adenosine kinase inhibitors. 5. Synthesis, enzyme inhibition, and analgesic activity of diaryl-erythro-furanosyltubercidin analogues," *Journal of Medicinal Chemistry*, vol. 48, No. 20 (2005) pp. 6430-6441.
Brown, Pamela, et al., "Molecular recognition of tyrosinyl adenylate analogues by prokaryotic tyrosyl tRNA synthetases," *Bioorganic & Medicinal Chemistry*, vol. 7 (1999) pp. 2473-2485.
Crimmins, Michael T., et al., "An efficient, general asymmetric synthesis of carbocyclic nucleosides: application of an asymmetric aldol/ring-closing metathesis strategy," *Journal of Organic Chemistry*, vol. 65, No. 25 (2000) pp. 8499-8509.
Gosselin, Gilles, et al., "A short and novel synthesis of carbocyclic nucleosides and 4'-epicarbocyclic nucleosides from 2-cyclopenten-1-ones," *Tetrahedron*, vol. 62 (2006) pp. 906-914.
Gough, Geoffrey R., et al., "New inhibitors of platelet aggregation. 5'-phosphate, 5'-phosphorothioate, and 5'-O-sulfamoyl derivatives of 2-substituted adenosine analogues," *Journal of Medicinal Chemistry*, vol. 21, No. 6 (1978) pp. 520-525.
Huang, Danny T., et al., "Structural basis for recruitment of Ubc12 by an E2 binding domain in NEDD8's E1," *Molecular Cell*, vol. 17 (Feb. 4, 2005) pp. 341-350.
Kristinsson, Haukur, et al., "A novel synthesis of sulfamoyl nucleosides," *Tetrahedron*, vol. 50, No. 23 (1994) pp. 6825-6838.

Kristinsson et al: "Herbicidally Active Sulfamoyl Nucleosides. Isolation and synthesis" ACS Symposium Series, 584 (Synthesis and Chemistry of Agrochemicals IV), pp. 206-219 (1995).
Kuang, Rongze, et al., Enantioselective syntheses of carbocyclic ribavirin and its analogs: linear versus convergent approaches, *Tetrahedron Letters*, vol. 41 (2000) pp. 9575-9579.
Lee, Jeewoo, et al., "N-alkoxysulfamide, N-hydroxysulfamide, and sulfamate analogues of methionyl and isoleucyl adenylates as inhibitors of methionyl-tRNA and isoleucyl-tRNA synthetases," *Bioorganic & Medicinal Chemistry Letters*, vol. 13 (2003) pp. 1087-1092.
Madhavan, G.V. Bindu, et al., "Synthesis and antiviral evaluation of 6'-substituted aristeromycins: potential mechanism-based inhibitors of S-adenosylhomocysteine hydrolase," *Journal of Medicinal Chemistry*, vol. 31 (1988) pp. 1798-1804.
Meillon, J.-C., et al., "Rapid access to 2'-branched-carbocyclic nucleosides and their 4'-epimers from 2-alkyl-cyclopentene-1-ones," *Nucleosides, Nucleotides, and Nucleic Acids*, vol. 24, No. 5-7 (2005) pp. 695-699.
Morizawa, Yoshitomi, et al., "Stereoselective introduction of fluorine atom: synthesis of racemic carbocyclic analogues of 3'-deoxy-3'-fluororibofuranosides and 3'-deoxy-3'-fluoroarabinofuranosides," *Bulletin of the Chemical Society of Japan*, vol. 66, No. 9 (1993) pp. 2714-2719.
Cancer Drug Design and Discovery Neidle, Stephen, ed. (Elsevier/Academic Press, 2008) pp. 427-431.
Pan, Zhen-Qiang, et al., "Nedd8 on cullin: building an expressway to protein destruction," *Oncogene*, vol. 23 (2004) pp. 1985-1997.
Peterson, Eileen M., et al., "Synthesis and biological evaluation of 5'-sulfamoylated purinyl carbocyclic nucleosides," *Journal of Medicinal Chemistry*, vol. 35, No. 22 (1992) pp. 3991-4000.
Shuman, Dennis A., et al., "The synthesis of nucleoside sulfamates related to nucleocidin," *Journal of the American Chemical Society*, vol. 92, No. 11 (Jun. 3, 1970) pp. 3434-3440.
Somu, Ravindranadh V., et al., "Rationally designed nucleoside antibiotics that inhibit siderophore biosynthesis of *Mycobacterium tuberculosis*," *Journal of Medicinal Chemistry*, vol. 49, No. 1 (2006) pp. 31-34.
Sugiyama, Hiroshi, et al., "Bleomycin-mediated degradation of aristeromycin-containing DNA. Novel dehydrogenation activity of iron(II)-bleomycin," *Journal of the American Chemical Society*, vol. 113 (1991) pp. 2290-2295.
Toyota, Akemi, et al., "Synthesis of 9-(C-5-hydroxy-C-4-hydroxymethylcyclopent-2-EN-R-1-YL)-9Hadenine [(+)-epinor-BCA]," *Heterocycles*, vol. 38, No. 1 (1994) pp. 27-30.
Trost, Barry M., et al., "A novel Pd-catalyzed cycloalkylation to isoxazoline 2-oxides. Application for the asymmetric synthesis of carbanucleosides," *Journal of the American Chemical Society*, vol. 114 (1992) pp. 8745-8747.
Ubukata, Makoto, et al., "Total synthesis of nucleoside antibiotic, ascamycin," *Tetrahedron Letters*, vol. 27, No. 33 (1986) pp. 3907-3908.
Ubukata, Makoto, et al., "Synthesis and biological activity of aminoacyl analogs of ascamycin," *Agricultural and Biological Chemistry*, vol. 52, No. 5 (1988) pp. 1117-1122.
Ugarkar, Bheemarao G., et al., "Adenosine kinase inhibitors. 3. Synthesis, SAR, and anti-inflammatory activity of a series of L-lyxofuranosyl nucleosides," *Journal of Medicinal Chemistry*, vol. 46, No. 22 (2003) pp. 4750-4760.
Vanhessche, K., et al., "Total synthesis of (−)-neplanocin A from L-ribulose," *Synlett*, vol. 12 (Dec. 1991) pp. 921-922.
Vince, Robert, et al., "The synthesis and biological evaluation of sulfamoyl nucleosides related to carbovir and AZT," *Nucleosides & Nucleotides*, vol. 14, Nos. 9 & 10 (1995) pp. 2051-2060.
Wachtmeister, Johanna, et al., "Synthesis of 4-substituted carbocyclic 2,3-dideoxy-3-Chydroxymethyl nucleoside analogues as potential anti-viral agents," *Tetrahedron*, vol. 55 (1999) pp. 10761-10770.
Winum, Jean-Yves, et al., "Sulfamates and their therapeutic potential," *Medicinal Research Reviews*, vol. 25, No. 2 (2005) pp. 186-228.
International Search Report with Written Opinion dated Jul. 17, 2006 from PCT/US06/004637 corresponding to U.S. Appl. No. 11/346,469.

(56) References Cited

OTHER PUBLICATIONS

International Search Report of the European Patent Office dated Aug. 3, 2007 issued in International Application No. PCT/US2007/002560.
Office Action dated Jan. 23, 2009 in U.S. Appl. No. 11/346,469.
Office Action dated Jul. 9, 2009 in U.S. Appl. No. 11/346,469.
Office Action dated Jan. 7, 2010 in U.S. Appl. No. 11/346,469.
Office Action dated Jan. 24, 2013 in U.S. Appl. No. 13/025,621.
Office Action dated Mar. 9, 2009 in U.S. Appl. No. 11/700,614.
Office Action dated Sep. 14, 2009 in U.S. Appl. No. 11/700,614.
Advisory Action dated Dec. 14, 2009 in U.S. Appl. No. 11/700,614.
Terminal Disclaimer and Supplemental Reply filed Feb. 11, 2010 in U.S. Appl. No. 11/700,614.
Office Action dated Apr. 1, 2013 in U.S. Appl. No. 13/526,946.
Frank Seela et al.: "The Isomeric 4-amino-N-methylpyrrolo[2,3-d]pyrimidines" Chemische Berichte, vol. 114, No. 6, pp. 2056-2063, XP002511148 examples 2c,2d (1981).
Holy, A. "Preparation of substituted (±)-5t-hydroxymethyl-3t-aminocyclopentane-1r,2c-diol derivatives related to carbocyclic ribonucleoside analogues." Collection of Czechoslovak Chemical Communications, vol. 41, No. 2, pp. 647-665 (1976).
International Search Report of the European Patent Office dated Jan. 20, 2009 issued in International Application No. PCT/US2008/009338.
James L. Kelley et al.: "Synthesis and anticonvulsant activity of N-Benzylpyrrolo[2,3-d]-,-pyrazolo[3,4-d]-, and -triazolo[4,5-d]pyrimidines: imidazole ring-modified analogues of 9-(2-Fluorobenzyl)-6-(methylamino)-9Hpurine," Journal of Medicinal Chemistry,vol. 38, No. 19, pp. 3884-3888, XP002511150 scheme 1 (1995).
Authelin et al: "Thermodynamics of non-stoichiometric pharmaceutical hydrates", International Journal of Pharmaceuticals, Elsevier BV, NL, vol. 303, No. 1-2, Oct. 13, 2005, pp. 37-53, XP027624197, ISSN: 0378-5173.
Khankari R K et al: "Pharmaceutical Hydrates", Thermochinica Acta, Elsevier Science Publishers, Amsterdam, NL, vol. 248, Jan. 1, 1995, pp. 61-79, SP001162001, ISSN: 0040-6031, DOI: 10.1016/0040-6031(95)91952-d.

* cited by examiner

HYDROCHLORIDE SALT OF((1S,2S,4R)-4-{4-[(1S)-2,3-DIHYDRO-1H-INDEN-1-YLAMINO]-7H-PYRROLO[2,3-D]PYRIMIDIN-7-YL}-2-HYDROXYCYCLOPENTYL)METHYL SULFAMATE

PRIORITY

This application claims the benefit under 35 U.S.C. §119(e) of U.S. Provisional Patent Application Ser. No. 61/216,221, filed May 14, 2009, incorporated by reference in its entirety.

FIELD

The present invention relates to the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate (I):

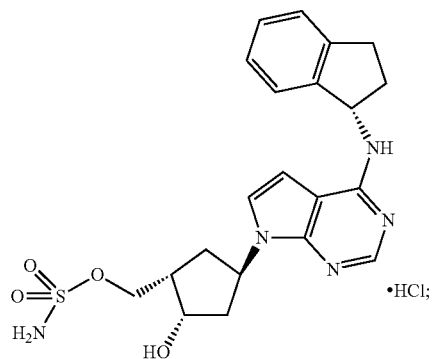

crystalline forms thereof, and solvates thereof.

The invention also relates to a process for the synthesis of the compound of formula (I). The invention also relates to the pharmaceutical use of the compound as an E1 activating enzyme inhibitor, crystalline forms thereof, and pharmaceutical compositions comprising the compound of formula (I).

BACKGROUND

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE, NAE, and SAE, as regulators of diverse cellular functions, are potentially important therapeutic targets for the identification of novel approaches to treatment of diseases and disorders.

Langston S. et al., Intl. App. Pub. No. WO 07/092,213 and Langston S. et al., U.S. App. Pub. No. 2007/0191293, which are hereby incorporated by reference in their entirety, disclose compounds which are effective inhibitors of E1 activating enzymes, particularly NAE. The compounds are useful for inhibiting E1 activity in vitro and in vivo and are useful for the treatment of disorders of cell proliferation, particularly cancer, and other disorders associated with E1 activity. One class of compounds described in Langston et al. are 4-substituted ((1S,2S,4R)-2-hydroxy-4-{7H-pyrrolo[2,3-d]pyrimidin-7-yl}cyclopentyl)methyl sulfamates. Armitage I. et al., U.S. App. Pub. No. 2009/0036678, which is hereby incorporated by reference in its entirety, discloses methods for the preparation of ((1S,2S,4R)-2-hydroxy-4-{7H-pyrrolo[2,3-d]pyrimidin-7-yl}cyclopentyl)methyl sulfamates, including ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate. This compound has been reported to be a selective NAE inhibitor. See, e.g., Soucy, T. A., et al., Nature, 2009, 458, 732-737 (which refers to the compound as MLN4924).

These applications additionally disclose pharmaceutical compositions containing these compounds, and methods for the treatment or therapy of diseases, disorders, or conditions associated with E1 activating enzymes, particularly NAE, including proliferative diseases such as cancer.

((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (II) is described in Intl. App. Pub. No. WO 07/092,213, U.S. App. Pub. No. 2007/0191293, and U.S. App. Pub. No. 2009/0036678. The potassium salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate is disclosed in Intl. App. Pub. No. WO 07/092,213 and U.S. App. Pub. No. 2007/0191293.

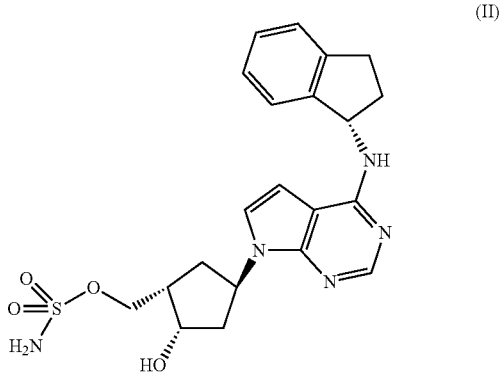 [SMILES: NS(=O)(=O)OC[C@@H]1C[C@@H](n2ccc3c(N[C@H]4CCc5ccccc54)ncnc32)C[C@@H]1O]
(II)

The large-scale manufacturing of a pharmaceutical composition poses many challenges to the chemist and chemical engineer. While many of these challenges relate to the handling of large quantities of reagents and control of large-scale reactions, the handling of the final product poses special challenges linked to the nature of the final active product itself. Not only should the product be prepared in high yield, be stable, and be capable of ready isolation, the product should possess properties that are suitable for the types of pharmaceutical preparations in which they are likely to be ultimately used. The stability of the active ingredient of the pharmaceutical preparation must be considered during each step of the manufacturing process, including the synthesis, isolation, bulk storage, pharmaceutical formulation and long-term storage. Each of these steps may be impacted by various environmental conditions of temperature and humidity.

The pharmaceutically active substance used to prepare the pharmaceutical compositions should be as pure as possible and its stability on long-term storage should be guaranteed under various environmental conditions. These properties are useful to prevent the appearance of unintended degradation products in pharmaceutical compositions, which degradation products may be potentially toxic or result simply in reducing the potency of the composition.

A primary concern for the large-scale manufacture of pharmaceutical compounds is that the active substance should have a stable crystalline morphology to ensure consistent processing parameters and pharmaceutical quality. If an unstable crystalline form is used, crystal morphology may change during manufacture and/or storage resulting in quality control problems and formulation irregularities. Such a change may affect the reproducibility of the manufacturing process and thus lead to final formulations which do not meet the high quality and stringent requirements imposed on formulations of pharmaceutical compositions. In this regard, it should be generally borne in mind that any change to the solid state of a pharmaceutical composition which can improve its physical and chemical stability gives a significant advantage over less stable forms of the same drug.

When a compound crystallizes from a solution or slurry, it may crystallize with different spatial lattice arrangements, a property referred to as "polymorphism." Each of the crystal forms is a "polymorph." While polymorphs of a given substance have the same chemical composition, they may differ from each other with respect to one or more physical properties, such as solubility, dissociation, true density, dissolution, melting point, crystal shape, compaction behavior, flow properties, and/or solid state stability.

As described generally above, the polymorphic behavior of drugs can be of great importance in pharmacy and pharmacology. The differences in physical properties exhibited by polymorphs affect practical parameters such as storage stability, compressibility and density (important in formulation and product manufacturing), and dissolution rates (an important factor in determining bio-availability). Differences in stability can result from changes in chemical reactivity (e.g., differential oxidation, such that a dosage form discolors more rapidly when it is one polymorph than when it is another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). In addition, the physical properties of the crystal may be important in processing: for example, one polymorph might be more likely to form solvates that cause the solid form to aggregate and increase the difficulty of solid handling, or might be difficult to filter and wash free of impurities (i.e., particle shape and size distribution might be different between one polymorph relative to other).

While drug formulations having improved chemical and physical properties are desired, there is no predictable means for preparing new drug forms (e.g., polymorphs) of existing molecules for such formulations. These new forms would provide consistency in physical properties over a range of environments common to manufacturing and composition usage. Thus, there is a need for new drug forms that are useful for inhibiting E1 activity in vitro and in vivo, and are useful for the treatment of disorders of cell proliferation, particularly cancer, and other disorders associated with E1 activity, as well as having properties suitable for large-scale manufacturing and formulation.

SUMMARY

The present invention relates to the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate of formula (I), crystalline forms thereof, and solvates thereof. These forms have properties that are useful for large-scale manufacturing, pharmaceutical formulation, and/or storage. The present invention also relates to a pharmaceutical composition comprising the Hydrochloride Salt, or a crystalline form thereof, or a solvate thereof; and to methods of use of the Hydrochloride Salt, or a crystalline form thereof, or a solvate thereof, for the treatment of a variety of diseases, disorders or conditions as described herein.

Some embodiments of the invention relate to the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I), wherein the Hydrochloride Salt is a crystalline form, the possible crystalline forms being described herein.

Some embodiments of the invention relate to a pharmaceutical composition comprising a pharmaceutically acceptable carrier or diluent; and the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I), or a crystalline form thereof, or a solvate thereof.

Some embodiments of the invention relate to said pharmaceutical compositions, wherein the Hydrochloride Salt is a crystalline form, the possible crystalline forms being described herein.

Some embodiments of the invention relate to methods of treating a subject in need of a E1 activating enzyme inhibitor, e.g., a subject with cancer, by administering an effective amount of the hydrochloride salt of ((1S,2S,4R)-4-{4-[(1S)-

2,3-dihydro-1H-inden-1-ylamino]-7H-pyrrolo[2,3-d]pyrimidin-7-yl}-2-hydroxycyclopentyl)methyl sulfamate (I), or a crystalline form thereof, or a solvate thereof. Some embodiments of the invention relate to said methods, wherein the Hydrochloride Salt is a crystalline form, the possible crystalline forms being described herein.

Some embodiments of the invention relate to methods of preparing the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I), or a crystalline form thereof, or a solvate thereof. Some embodiments of the invention are directed to said methods, wherein the Hydrochloride Salt is a crystalline form, the possible crystalline forms being described herein.

The present invention shall be more fully discussed with the aid of the following figures and detailed description below.

BRIEF DESCRIPTION OF THE DRAWINGS

In the descriptions that follow, "XRPD" means X-ray powder diffraction, "DSC" means differential scanning calorimetry, and "TGA" means thermal gravimetric analysis.

DETAILED DESCRIPTION

Definitions and Abbreviations

As used above, and throughout the description, the following terms, unless otherwise indicated, shall be understood to have the following meanings.

The terms "Hydrochloride Salt" and "HCl Salt" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate.HCl" are used interchangeably, and describe the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, that has the structure of formula (I).

Figure 1:
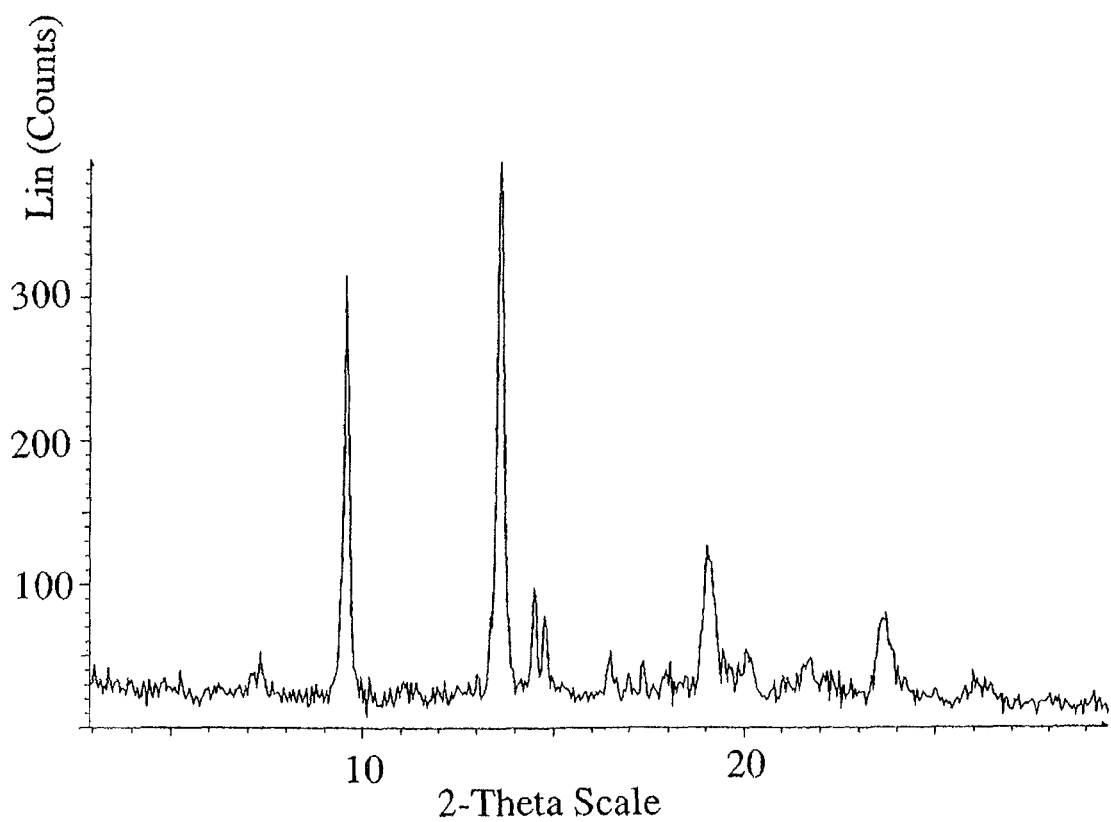
FIG. 1 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1.
Figure 2:
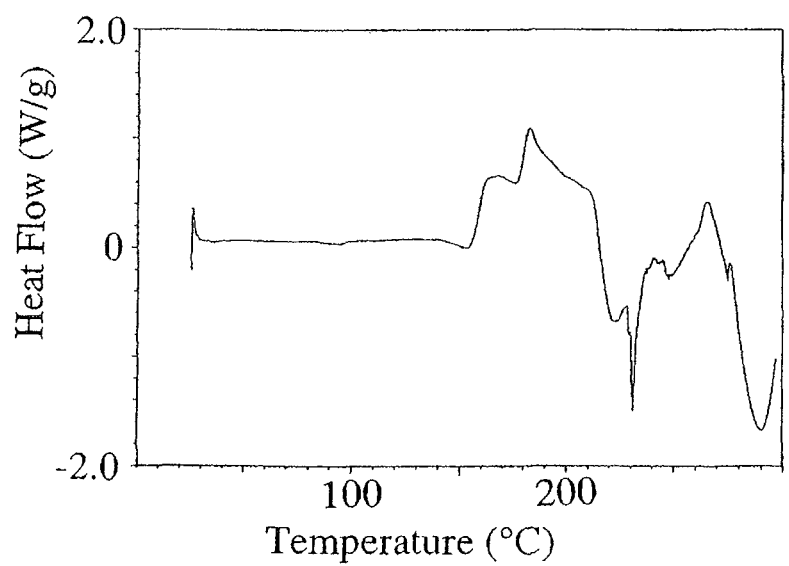
FIG. 2 is a DSC profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1.
Figure 3:
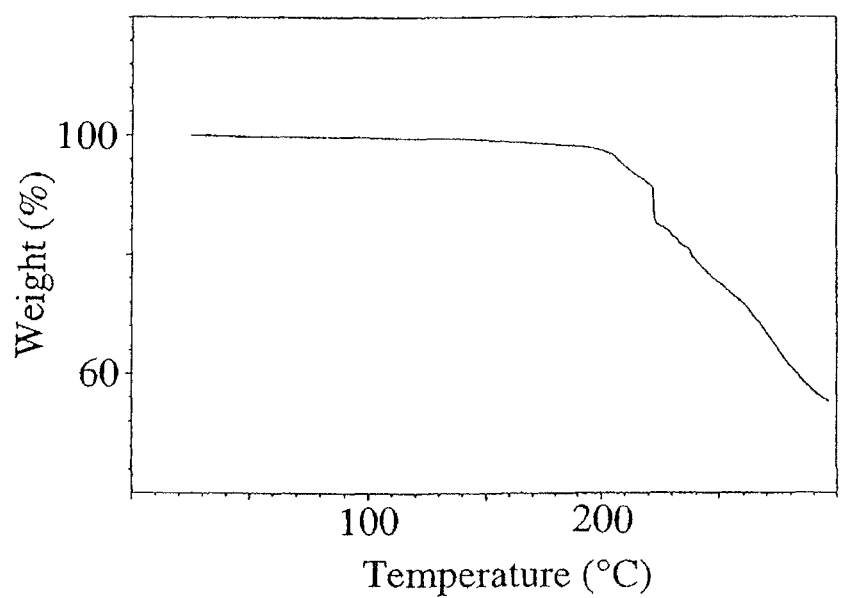
FIG. 3 is a TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1.

The terms "Form 1" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1" are used interchangeably, and describe Form 1 of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, as characterized in some embodiments by the data shown in FIGS. 1, 2 and 3.

Figure 4:
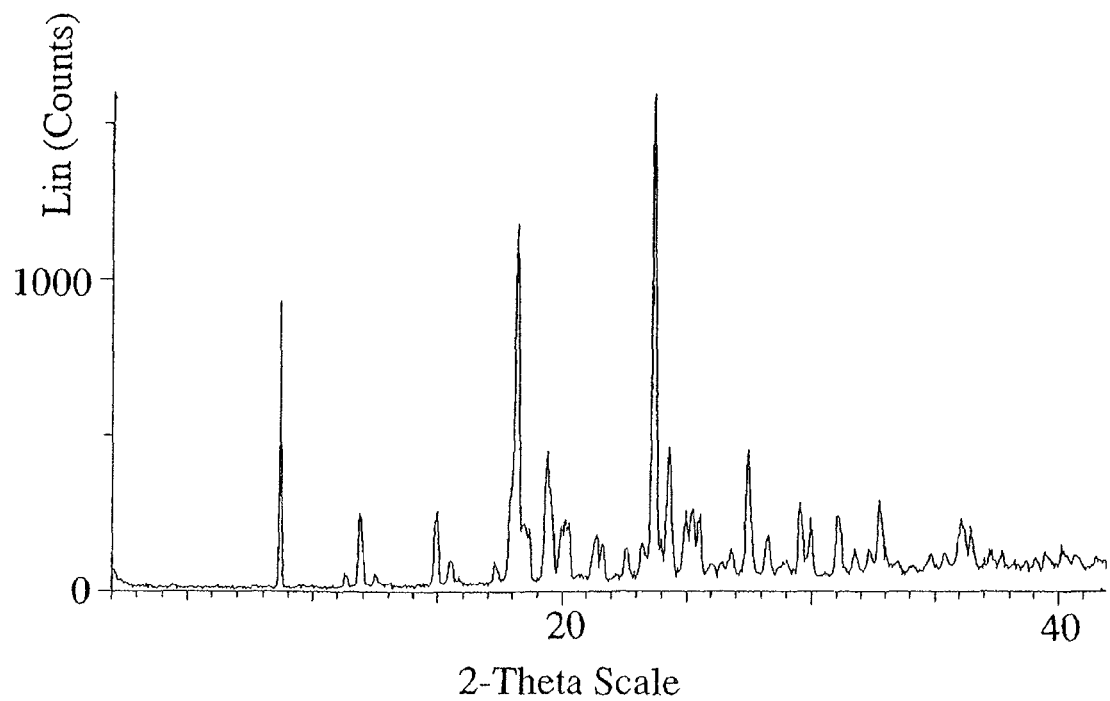
FIG. 4 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 2.
Figure 5:
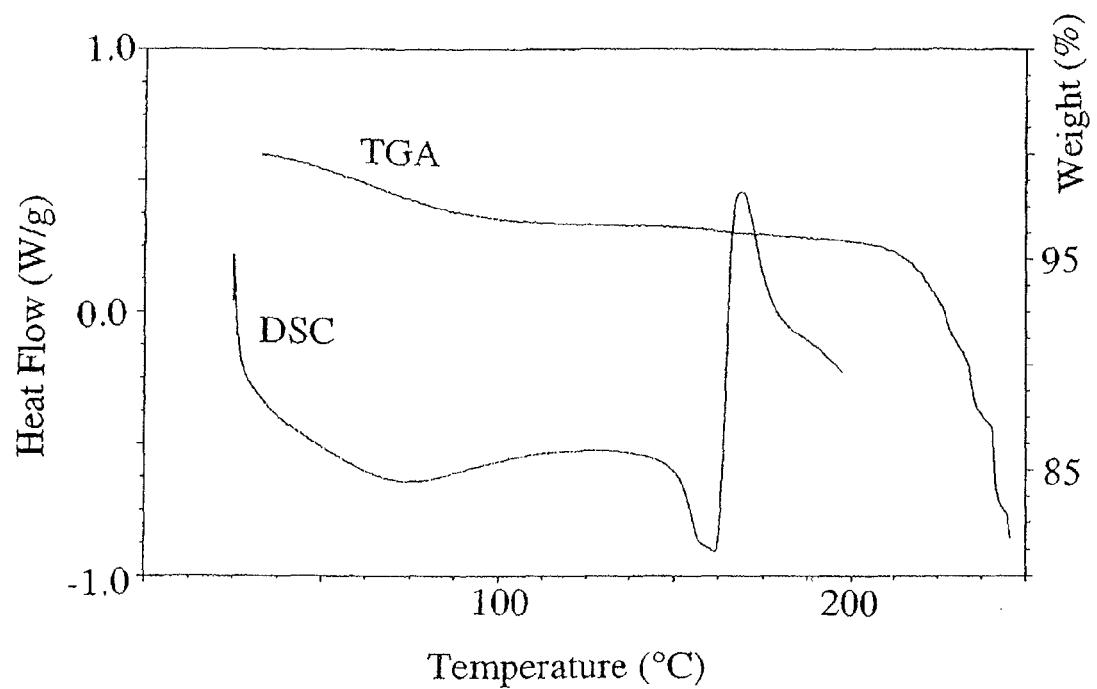
FIG. 5 is a DSC/TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 2.

The terms "Form 2" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 2" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride hydrate" are used interchangeably and describe Form 2 as a hydrate of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, as characterized in some embodiments by data shown in FIGS. 4 and 5.

Figure 6:
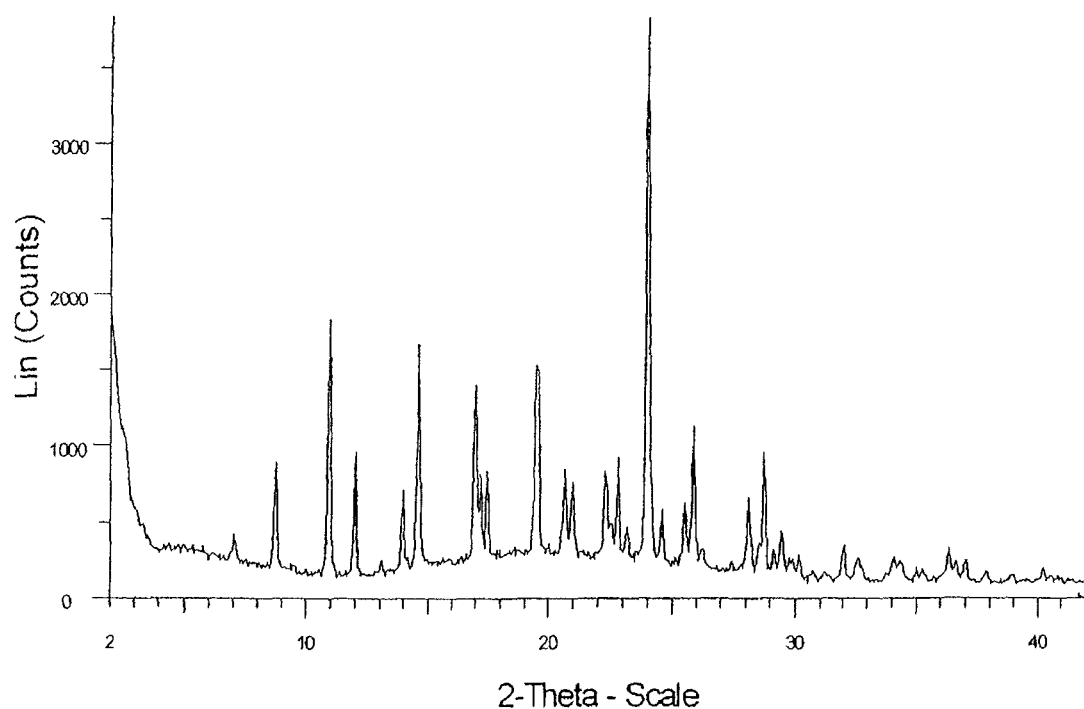
FIG. 6 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3A.
Figure 7:
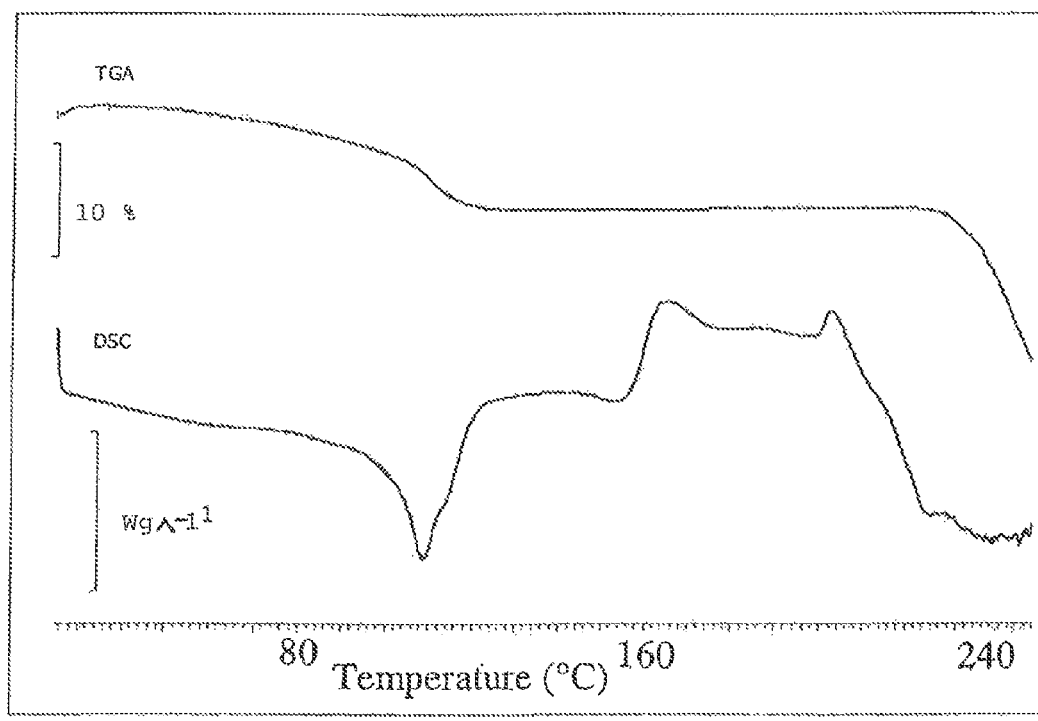
FIG. 7 is a DSC/TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3A.

The terms "Form 3A" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3A" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride ethanol solvate" are used interchangeably and describe Form 3A as an ethanol solvate of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, as characterized in some embodiments by data shown in FIGS. 6 and 7.

Figure 8:
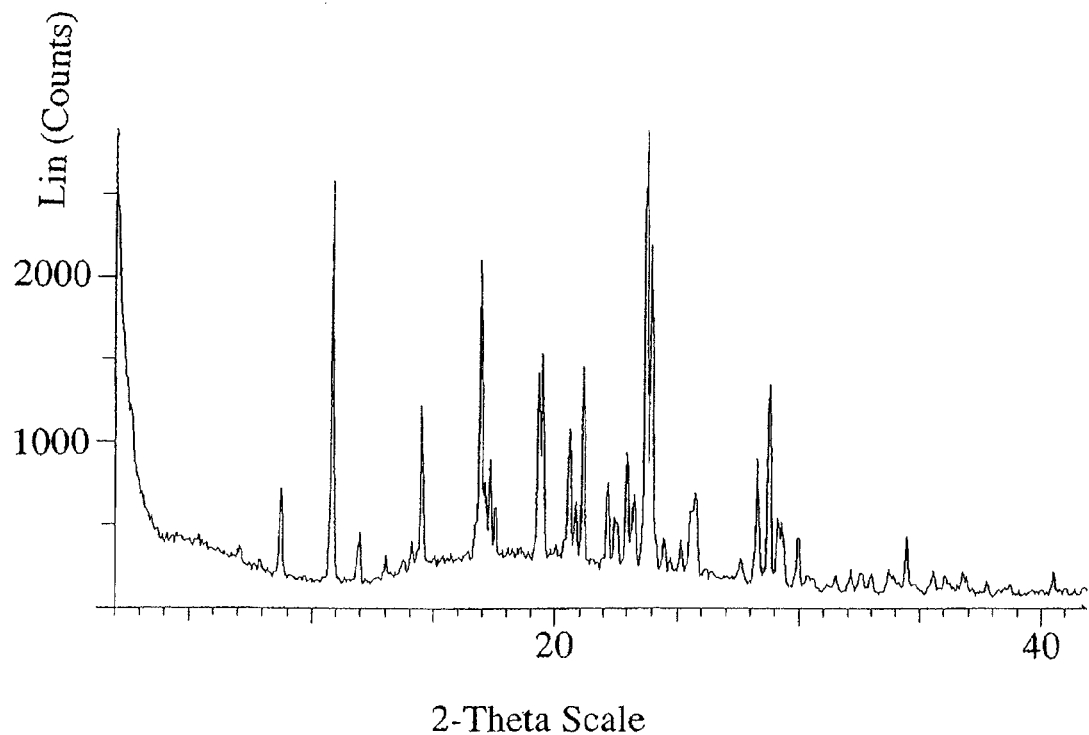
FIG. 8 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3B.
Figure 9:
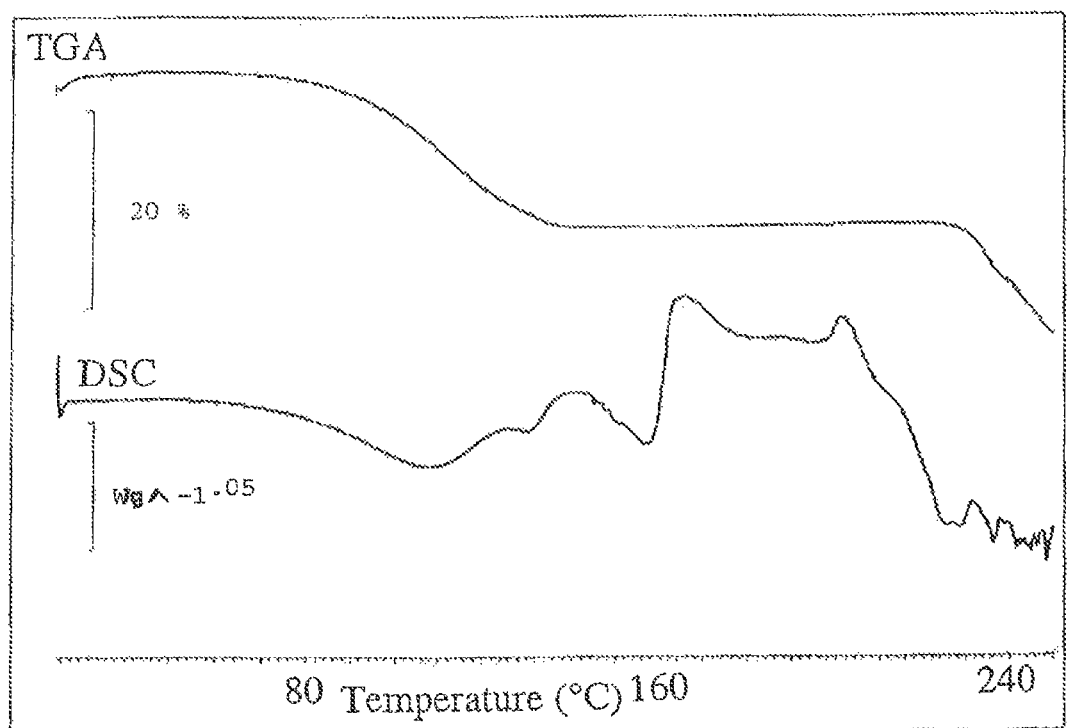
FIG. 9 is a DSC/TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3B.

The terms "Form 3B" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3B" and "((1S,2S,4R)-4-{4-[(1S)-2,3-dihydro- 1H-inden-1-ylamino]-7H-pyrrolo[2,3-d]pyrimidin-7-yl}-2-hydroxycyclopentyl)methyl sulfamate hydrochloride ethyl acetate solvate" are used interchangeably and describe Form 3B as an ethyl acetate solvate of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, as characterized in some embodiments by data shown in FIGS. 8 and 9.

Figure 10:
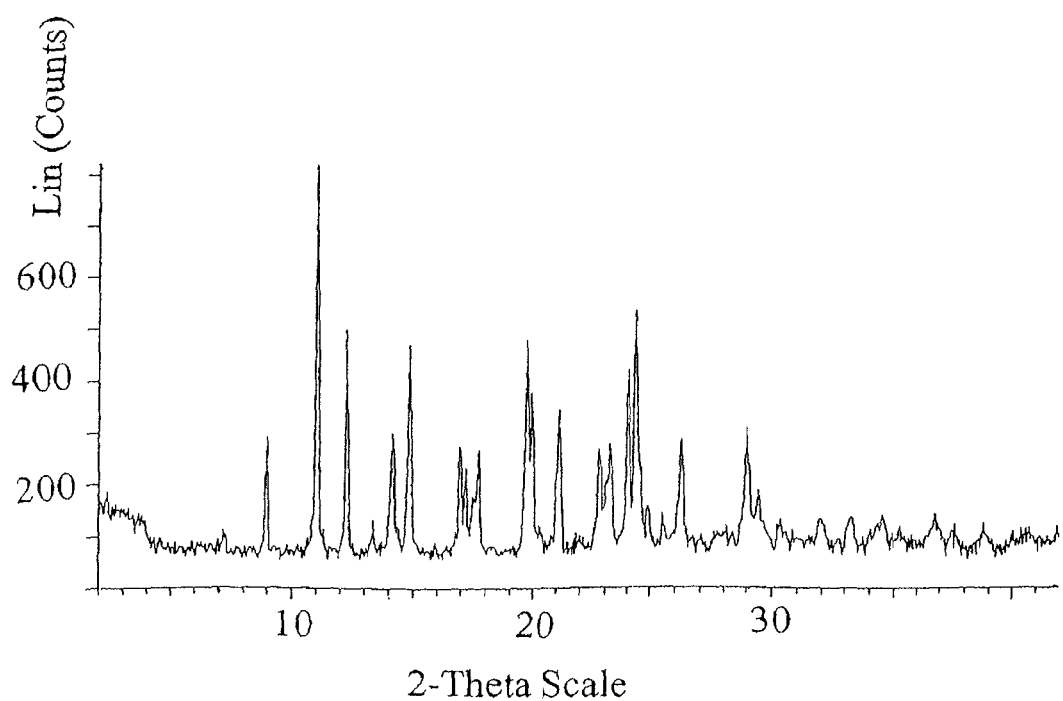
FIG. 10 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3C.
Figure 11:
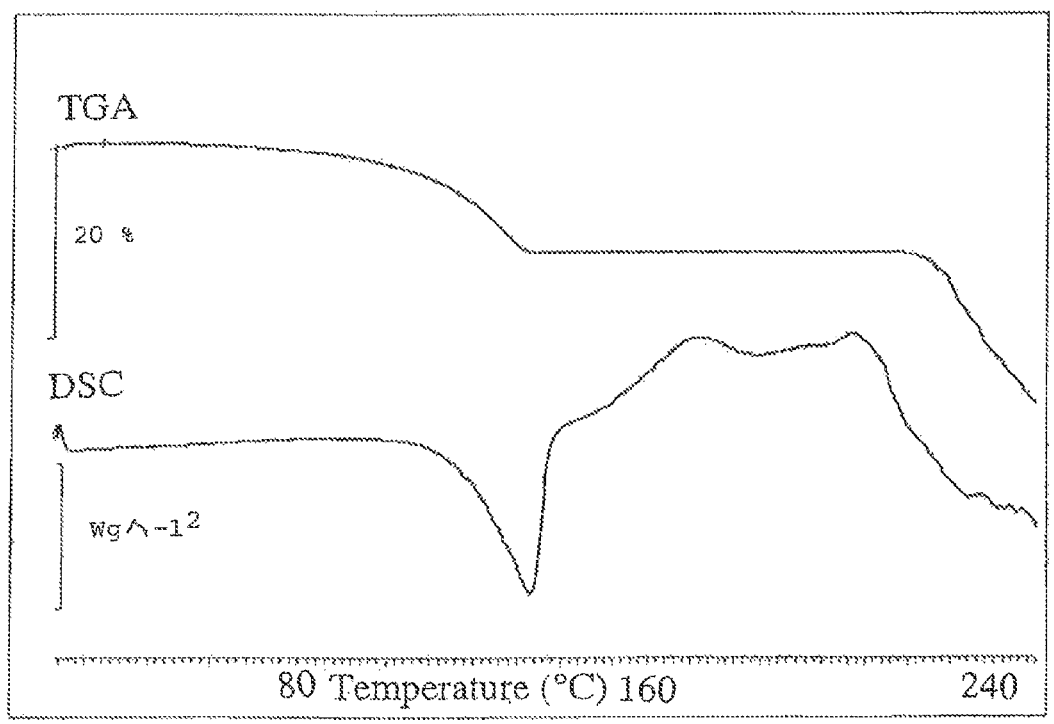
FIG. 11 is a DSC/TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3C.

The terms "Form 3C" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3C" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride methyl ethyl ketone solvate" are used interchangeably and describe Form 3C as an methyl ethyl ketone solvate of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, as characterized in some embodiments by data shown in FIGS. 10 and 11.

Figure 12:
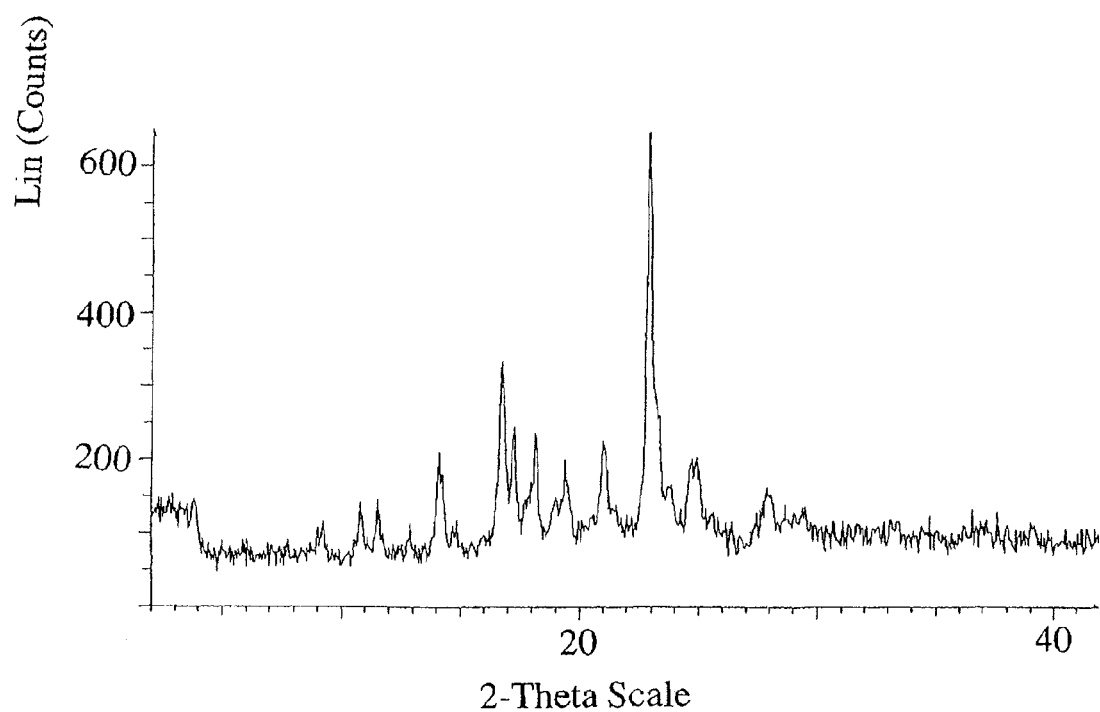
FIG. 12 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 5.
Figure 13:
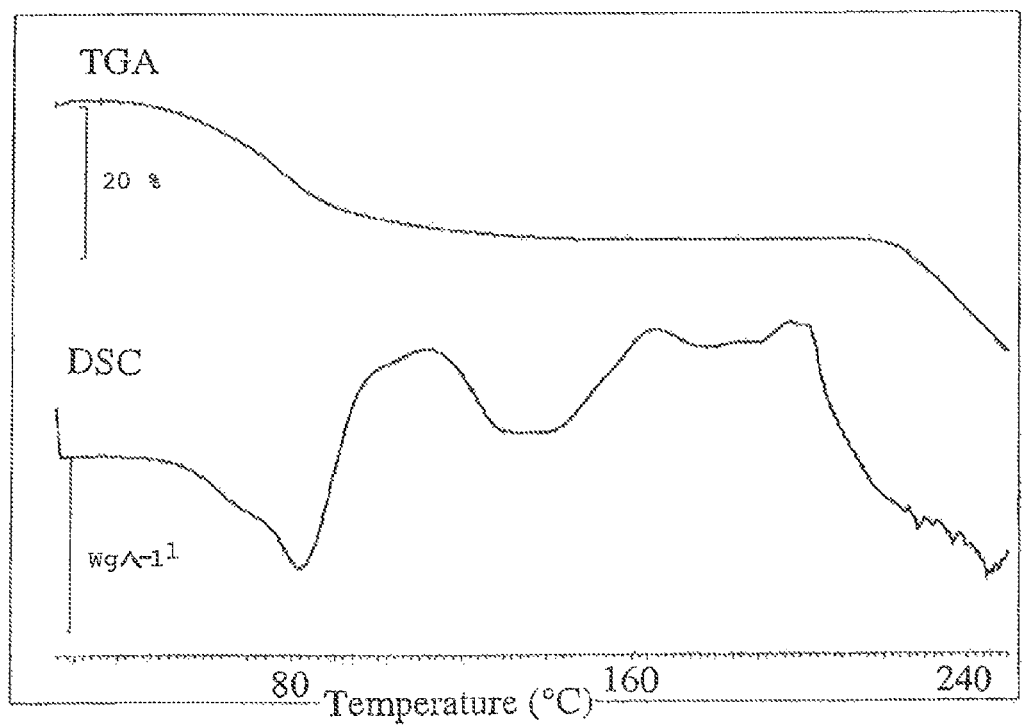
FIG. 13 is a DSC/TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 5.

The terms "Form 5" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 5" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride tetrahydrofuran solvate" are used interchangeably and describe Form 5 as a tetrahydrofuran solvate of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, as characterized in some embodiments by data shown in FIGS. 12 and 13.

Figure 14:
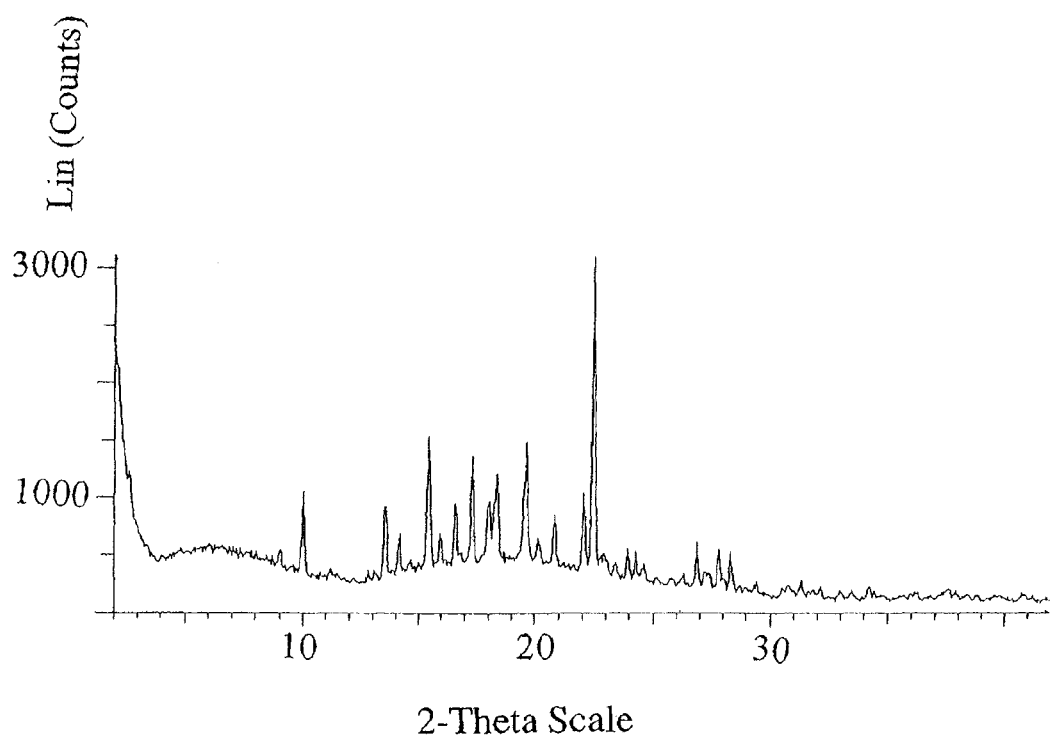
FIG. 14 is an XRPD pattern of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 7.
Figure 15:
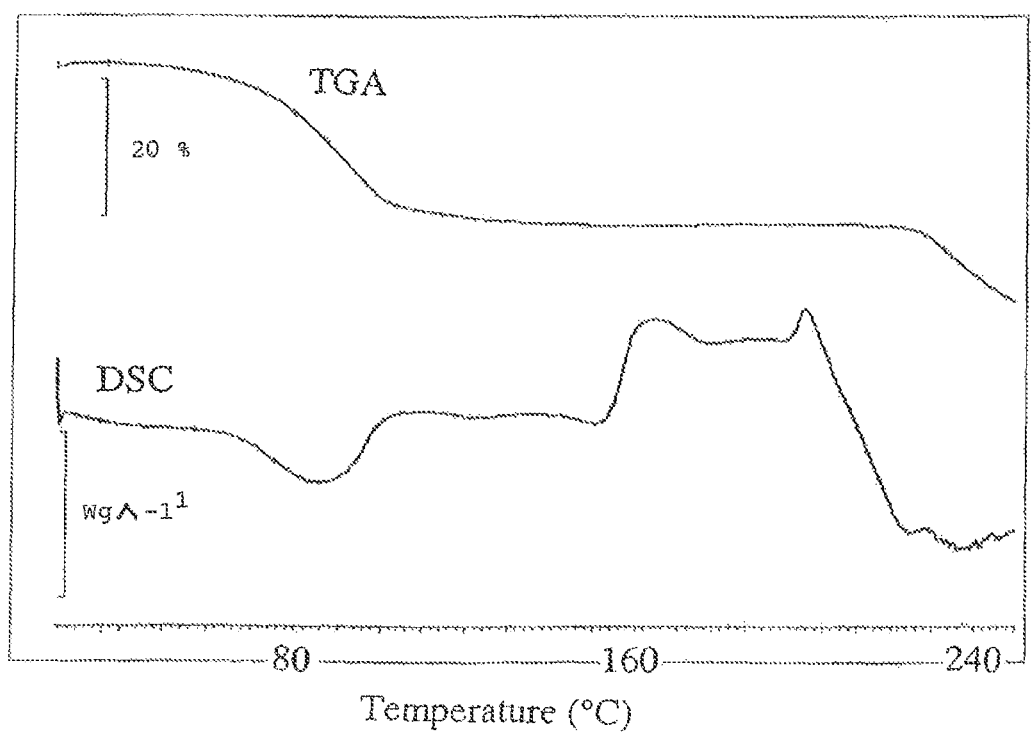
FIG. 15 is a DSC/TGA profile for ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 7.

The terms "Form 7" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 7" and "((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride dioxane solvate" are used interchangeably and describe Form 7 as a dioxane solvate of the hydrochloride salt of ((1S,2S,4R)-4-{4-[(1S)-2,3-dihydro-1H-inden-1-ylamino]-1-7H-pyrrolo[2,3-d]pyrimidin-7-yl}-2-hydroxycyclopentyl)methyl sulfamate, as characterized in some embodiments by data shown in FIGS. 14 and 15.

As used herein, "crystalline" refers to a solid in which the constituent atoms, molecules, or ions are packed in a regularly ordered, repeating three-dimensional pattern having a highly regular chemical structure. In particular, a crystalline Hydrochloride Salt may be produced as one or more crystalline forms of the Hydrochloride Salt. For the purposes of this application, the terms "crystalline form" and "polymorph" are synonymous; the terms distinguish between crystals that have different properties (e.g., different XRPD patterns, different DSC scan results). Pseudopolymorphs are typically different solvates of a material, and thus their properties differ from one another. Thus, each distinct polymorph and pseudopolymorph of the Hydrochloride Salt is considered to be a distinct crystalline form herein.

"Substantially crystalline" refers to Hydrochloride Salts that are at least a particular weight percent crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to Hydrochloride Salts that are at least 70% crystalline. In some embodiments, substantially crystalline refers to Hydrochloride Salts that are at least 80% crystalline. In some embodiments, substantially crystalline refers to Hydrochloride Salts that are at least 85% crystalline. In some embodiments, substantially crystalline refers to Hydrochloride Salts that are at least 90% crystalline. In some embodiments, substantially crystalline refers to Hydrochloride Salts that are at least 95% crystalline.

The term "solvate or solvated" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, hydrates, ethanolates, and methanolates.

The term "hydrate" refers to a solvate wherein the solvent molecule is $H_2O$ that is present in a defined stoichiometric amount, and includes, for example, hemihydrates, monohydrates, dihydrates, and trihydrates.

The term "mixture" refers to the combined elements of the mixture regardless of the phase-state of the combination (e.g., liquid or liquid/crystalline).

The term "seeding" refers to the addition of crystalline material to a solution or mixture to initiate crystallization.

In one aspect, the present invention is related to the hydrochloride salt of the compound ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate, or a crystalline form thereof, or a solvate thereof. Accordingly, the present invention provides a compound (I):

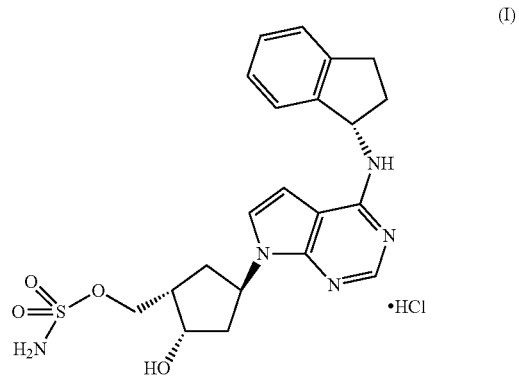 [SMILES: NS(=O)(=O)OC[C@@H]1C[C@@H](n2ccc3c(N[C@H]4CCc5ccccc54)ncnc32)C[C@@H]1O ; Cl]

or a crystalline form thereof, or a solvate thereof.

Provided herein is an assortment of characterizing information to describe the crystalline forms of the hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I). It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

The Hydrochloride Salt has properties that make it suitable for large-scale pharmaceutical formulation manufacture. In contrast to the potassium salt of ((1S,2S,4R)-4-{4-[(1S)-2,3-dihydro-1H-inden-1-ylamino]-7H-pyrrolo[2,3-d]pyrimidin- 7-yl}-2-hydroxycyclopentyl)methyl sulfamate, which was found to be only partially crystalline, the Hydrochloride Salt exists in distinct crystalline forms which are described herein, thus providing consistency of physical properties. Further, Form 1 and Form 2 of the Hydrochloride Salt exhibit increased stability on storage over the potassium salt of ((1S, 2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate.

Some embodiments of the invention are directed to the Hydrochloride Salt, wherein at least a particular percentage by weight of the Hydrochloride Salt is crystalline. In some embodiments, the Hydrochloride Salt is substantially crystalline. Non-limiting examples of a crystalline or substantially crystalline Hydrochloride Salt include a crystalline form of the Hydrochloride Salt or a mixture of different crystalline forms. Some embodiments of the invention are also directed to a Hydrochloride Salt, wherein at least a particular percentage by weight of the Hydrochloride Salt is crystalline, that excludes one or more designated crystalline forms from a particular weight percentage of Hydrochloride Salt. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the Hydrochloride Salt is crystalline, the remainder of the Hydrochloride Salt is the amorphous form of the Hydrochloride Salt.

Other embodiments of the invention are directed to the Hydrochloride Salt being a crystalline form, or being substantially a crystalline form. The crystalline form may be a particular percentage by weight of the crystalline Hydrochloride Salt. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the Hydrochloride Salt is a designated crystalline form, the remainder of the Hydrochloride Salt is some combination of the amorphous form of the Hydrochloride Salt, and one or more crystalline forms of the Hydrochloride Salt excluding the designated crystalline form. In some embodiments, the Hydrochloride Salt is at least 90% by weight of a crystalline form. In some embodiments, the Hydrochloride Salt is at least 95% by weight of a crystalline form. In some embodiments, the Hydrochloride Salt is at least 80% by weight of a crystalline form. In some embodiments, the Hydrochloride Salt is at least 85% by weight of a crystalline form.

In the following description of the Hydrochloride Salt, embodiments of the invention may be described with reference to a particular crystalline form of the Hydrochloride Salt, as characterized by one or more properties as discussed herein. The descriptions characterizing the crystalline forms may also be used to describe the mixture of different crystalline forms that may be present in a crystalline Hydrochloride Salt. However, the particular crystalline forms of the Hydrochloride Salt may also be characterized by one or more of the characteristics of the polymorph as described herein, with or without regard to referencing a particular crystalline form.

Throughout the specification and claims, when a crystalline form of the Hydrochloride Salt is identified using one or more XRPD peaks given as angles 2θ, each of the 2θ values is understood to mean the given value ±0.2 degrees.

Throughout the specification and claims, when a crystalline form of the Hydrochloride Salt is identified using one or more temperatures from a DSC profile (e.g., onset of endothermic transition, melt, etc.), each of the temperature values is understood to mean the given value±2° C.

Form 1

FIG. 1 shows an X-ray powder diffraction (XRPD) pattern of Form 1 of the Hydrochloride Salt obtained using CuKα radiation. Peaks identified in FIG. 1 include those listed in Table 1.

TABLE 1

| Angle 2θ° | Intensity % |
|---|---|
| 7.3 | 13.1 |
| 9.573 | 79.6 |
| 13.643 | 100 |
| 14.532 | 24.4 |
| 14.8 | 19.4 |
| 16.476 | 13.4 |
| 16.976 | 9.3 |
| 17.325 | 11.3 |
| 18.002 | 11.3 |
| 19.084 | 31.7 |
| 20.103 | 13.6 |
| 21.069 | 8.8 |
| 21.743 | 11.8 |
| 23.677 | 19.9 |

In some embodiments, Form 1 is characterized by an XRPD pattern having peaks at 2θ angles of 9.6°, 13.6° and 19.1°. In some embodiments, Form 1 is characterized by an XRPD pattern having peaks at 2θ angles of 9.6°, 13.6°, 14.5°, 19.1° and 23.7°. In some embodiments, Form 1 is characterized by an XRPD pattern having peaks at 2θ angles of 7.3°, 9.6°, 13.6°, 14.5°, 14.8°, 16.5°, 17.0°, 17.3°, 18.0°, 19.1°, 20.1°, 21.1°, 21.7° and 23.7°. In some embodiments, Form 1 is characterized by an XRPD pattern substantially as shown in FIG. 1.

FIG. 2 shows a differential scanning calorimetry (DSC) profile of Form 1 of the Hydrochloride Salt. The DSC graph plots the heat flow as a function of temperature from a sample, the temperature rate change being about 10° C./min. In some embodiments, Form 1 is characterized by a DSC profile substantially as shown in FIG. 2.

FIG. 3 shows a thermal gravimetric analysis (TGA) profile of Form 1 of the Hydrochloride Salt. The TGA profile plots the percent loss of weight of the sample as a function of temperature, the temperature rate change being about 10° C./min. In some embodiments, Form 1 is characterized by a TGA profile substantially as shown in FIG. 3.

Form 1 of the Hydrochloride Salt described herein has a solubility of about 7.8 mg/mL in water. The resulting solution has a pH of about 2.33.

In some embodiments, Form 1 is characterized by at least two of the following features (I-i)-(I-iv):

(I-i) an XRPD pattern having peaks at 2θ angles of 9.6°, 13.6° and 19.1°;

(I-ii) a DSC profile substantially as shown in FIG. 2;

(I-iii) a TGA profile substantially as shown in FIG. 3;

(I-iv) a solubility of about 7.8 mg/mL in water.

In some embodiments, Form 1 is characterized by at least three of the features (I-i)-(I-iv). In some embodiments, Form 1 is characterized by at least one of the features (I-ii)-(I-iv) and by feature (I-v) an XRPD pattern having peaks at 2θ angles of 9.6°, 13.6°, 14.5°, 19.1° and 23.7°

Form 2

FIG. 4 shows an XRPD pattern of Form 2 of the Hydrochloride Salt obtained using CuKα radiation. Peaks identified in FIG. 4 include those listed in Table 2.

TABLE 2

| Angle 2θ° | Intensity % |
|---|---|
| 8.66 | 58.2 |
| 11.32 | 3.6 |
| 11.86 | 15.4 |
| 12.46 | 3.5 |
| 14.91 | 14.5 |
| 15.52 | 6.1 |
| 17.29 | 5.8 |
| 18.16 | 73.9 |
| 18.50 | 13.8 |
| 18.70 | 12.4 |
| 19.41 | 28.0 |
| 19.95 | 13.0 |
| 20.12 | 14.2 |
| 20.31 | 13.9 |
| 21.39 | 11.1 |
| 21.67 | 9.9 |
| 22.62 | 8.4 |
| 23.27 | 9.8 |
| 23.75 | 100 |
| 24.01 | 10.5 |
| 24.33 | 28.8 |
| 25.00 | 16.2 |
| 25.28 | 16.4 |
| 25.61 | 15.6 |
| 26.82 | 8.3 |
| 27.51 | 28.4 |
| 28.25 | 11.1 |
| 28.93 | 5.8 |
| 29.59 | 17.6 |
| 30.00 | 15.0 |
| 31.09 | 15.4 |
| 32.80 | 18.3 |

In some embodiments, Form 2 is characterized by an XRPD pattern having peaks at 2θ angles of 8.7°, 18.2° and 23.8°. In some embodiments, Form 2 is characterized by an XRPD pattern having peaks at 2θ angles of 8.7°, 18.2°, 19.4°, 23.8°, 24.3° and 27.5°. In some embodiments, Form 2 is characterized by an XRPD pattern having peaks at 2θ angles of 8.7°, 11.3°, 11.9°, 12.5°, 14.9°, 15.5°, 17.3°, 18.2°, 18.5°, 18.7°, 19.4°, 20.0°, 20.1°, 20.3°, 21.4°, 21.7°, 22.6°, 23.3°, 23.8°, 24.0°, 24.3°, 25.0°, 25.3°, 25.6°, 26.8°, 27.5°, 28.3°, 28.9°, 29.6°, 30.0°, 31.1° and 32.8°. In some embodiments, Form 2 is characterized by an XRPD pattern substantially as shown in FIG. 4.

FIG. 5 shows a DSC profile of Form 2 of the Hydrochloride Salt. The DSC graph plots the heat flow as a function of temperature from a sample, the temperature rate change being about 10° C./min. In some embodiments, Form 2 is characterized by a DSC profile characterized by an endothermic transition with an onset temperature of 151° C. with a melt at 161.6° C., followed by a small exothermic transition with a melt at 169° C. In some embodiments, Form 2 is characterized by a DSC profile substantially as shown in FIG. 5.

FIG. 5 also shows a TGA profile of Form 2 of the Hydrochloride Salt. The TGA profile plots the percent loss of weight of the sample as a function of temperature, the temperature rate change being about 10° C./min. The weight loss shown in FIG. 5 represents a loss of about 3.4% of the weight of the sample as the temperature is changed from 25° C. to 125° C. In some embodiments, Form 2 is characterized by a TGA profile substantially as shown in FIG. 5.

In another embodiment of the invention, Form 2 is characterized by at least two of the following features (II-i)-(II-iii):

(II-i) an XRPD pattern having peaks at 2θ angles of 8.7°, 18.2° and 23.8;
(II-ii) a DSC profile substantially as shown in FIG. 5;
(II-iii) a TGA profile substantially as shown in FIG. 5.

In some embodiments, Form 2 is characterized by all three of the features (II-i)-(II-iii). In some embodiments, Form 2 is characterized by at least one of the features (II-ii) and (II-iii) and feature (II-iv) an XRPD pattern having peaks at 2θ angles of 8.7°, 18.2°, 19.4°, 23.8°, 24.3° and 27.5°.

Form 3A

FIG. 6 shows an XRPD pattern of Form 3A of the Hydrochloride Salt obtained using CuKα radiation. Peaks identified include those listed in Table 3.

TABLE 3

| Angle 2θ° | Intensity % |
|---|---|
| 6.97 | 14.5 |
| 8.69 | 26.9 |
| 10.87 | 53.4 |
| 11.99 | 29.9 |
| 13.05 | 10.8 |
| 13.94 | 26.2 |
| 14.59 | 51.9 |
| 16.88 | 48.3 |
| 17.24 | 30.9 |
| 17.48 | 28.5 |
| 19.51 | 67.8 |
| 20.71 | 32.5 |
| 20.95 | 30.7 |
| 22.34 | 30.2 |
| 22.79 | 30.7 |
| 23.11 | 18.0 |
| 23.98 | 100.0 |
| 24.60 | 21.3 |
| 25.53 | 21.6 |
| 25.90 | 35.8 |
| 28.06 | 23.1 |
| 28.46 | 12.2 |
| 28.72 | 25.7 |
| 29.08 | 11.4 |
| 29.41 | 16.0 |
| 32.00 | 11.9 |
| 32.72 | 10.5 |
| 34.14 | 9.2 |
| 34.36 | 8.3 |

In some embodiments, Form 3A is characterized by an XRPD pattern having peaks at 2θ angles of 10.9°, 14.6°, 19.5° and 24.0°. In some embodiments, Form 3A is characterized by an XRPD pattern having peaks at 2θ angles of 10.9°, 14.6°, 16.9°, 19.5°, 24.0° and 25.9°. In some embodiments, Form 3A is characterized by an XRPD pattern having peaks at 2θ angles of 7.0°, 8.7°, 10.9°, 12.0°, 13.0°, 13.9°, 14.6°, 16.9°, 17.2°, 17.5°, 19.5°, 20.7°, 21.0°, 22.3°, 22.8°, 23.1°, 24.0°, 24.6°, 25.5°, 25.9°, 28.1°, 28.5°, 28.7°, 29.1°, 29.4°, 32.0°, 32.7°, 34.1° and 34.4°. In some embodiments, Form 3A is characterized by an XRPD pattern substantially as shown in FIG. 6.

FIG. 7 shows a DSC profile of Form 3A of the Hydrochloride Salt. The DSC graph plots the heat flow as a function of temperature from a sample, the temperature rate change being about 10° C./min. In some embodiments, Form 3A is characterized by a DSC profile characterized by an endothermic transition that has an onset temperature of 99.9° C., with a melt at 108.8° C. In some embodiments, Form 3A is characterized by a DSC profile substantially as shown in FIG. 7.

FIG. 7 also shows a TGA profile of Form 3A of the Hydrochloride Salt. The TGA profile, plots the percent loss of weight of the sample as a function of temperature, the temperature rate change being about 10° C./min. The weight loss represents a loss of about 9.2% of the weight of the sample as the temperature is changed from 25° C. to 220° C. This corresponds to a loss of about 1.1 moles of ethanol, indicating Form 3A is a solvate. In some embodiments, Form 3A is characterized by a TGA profile substantially as shown in FIG. 7.

In some embodiments, Form 3A is characterized by at least two of the following features (III-i)-(III-iii):
(III-i) an XRPD pattern having peaks at 2θ angles of 10.9°, 14.6°, 19.5° and 24.0°;
(III-ii) a DSC profile substantially as shown in FIG. 7;
(III-iii) a TGA profile substantially as shown in FIG. 7.

In some embodiments, Form 3A is characterized by all three of the features (III-i)-(III-iii). In some embodiments, Form 3A is characterized by at least one of features (III-ii) and (III-iii) and feature (III-iv) an XRPD pattern having peaks at 2θ angles of 10.9°, 14.6°, 16.9°, 19.5°, 24.0° and 25.9°.

Form 3B

FIG. 8 shows an XRPD pattern of Form 3B of the Hydrochloride Salt obtained using CuKα radiation. Peaks identified in FIG. 8 include those listed in Table 4.

TABLE 4

| Angle 2θ° | Intensity % |
|---|---|
| 7.01 | 12.7 |
| 8.75 | 24.6 |
| 10.77 | 89.5 |
| 11.93 | 15.7 |
| 13.02 | 11 |
| 14.04 | 13.7 |
| 14.48 | 42.3 |
| 16.91 | 73 |
| 17.25 | 31 |
| 17.47 | 21.2 |
| 19.34 | 49.1 |
| 20.56 | 37.2 |
| 20.85 | 22.1 |
| 21.16 | 50.5 |
| 22.16 | 26.1 |
| 22.52 | 18.6 |
| 23.02 | 32.3 |
| 23.25 | 23.5 |
| 23.72 | 100 |
| 24.01 | 76 |
| 24.51 | 14.3 |
| 25.15 | 13.8 |
| 25.72 | 23.7 |
| 27.64 | 10.1 |
| 28.33 | 30.8 |
| 28.75 | 46.8 |
| 29.24 | 17.7 |
| 29.95 | 14.6 |
| 34.50 | 14.7 |
| 40.55 | 7.8 |

In some embodiments, Form 3B is characterized by an XRPD pattern having peaks at 2θ angles of 10.8°, 16.9°, 23.7° and 24.0°. In some embodiments, Form 3B is characterized by an XRPD pattern having peaks at 2θ angles of 10.8°, 14.5°, 16.9°, 19.3°, 21.2°, 23.7°, 24.0° and 28.8°. In some embodiments, Form 3B is characterized by an XRPD pattern having peaks at 2θ angles of 7.0°, 8.8°, 10.8°, 11.9°, 13.0°, 14.0°, 14.5°, 16.9°, 17.3°, 17.5°, 19.3°, 20.6°, 20.9°, 21.2°, 22.2°, 22.5°, 23.0°, 23.3°, 23.7°, 24.0°, 24.5°, 25.6°, 25.7°, 27.6°, 28.3°, 28.8°, 29.2°, 30.0°, 34.5° and 40.6°. In some embodiments, Form 3B is characterized by an XRPD pattern substantially as shown in FIG. 8.

FIG. 9 shows a DSC profile of Form 3B of the Hydrochloride Salt. The DSC graph plots the heat flow as a function of temperature from a sample, the temperature rate change being about 10° C./min. In some embodiments, Form 3B is characterized by a DSC profile substantially as shown in FIG. 9.

FIG. 9 also shows a TGA profile of Form 3B of the Hydrochloride Salt. The TGA profile, plots the percent loss of weight of the sample as a function of temperature, the temperature rate change being about 10° C./min. The weight loss represents a loss of about 15.7% of the weight of the sample as the temperature is changed from 25° C. to 250° C. This corresponds to a loss of about 1 mole of ethyl acetate, indicating Form 3B is a solvate. In some embodiments, Form 3B is characterized by a TGA profile substantially as shown in FIG. 9.

In some embodiments, Form 3B is characterized by at least two of the following features (IV-i)-(IV-iii):
(IV-i) an XRPD pattern having peaks at 2θ angles of 10.8°, 16.9°, 23.7° and 24.0°;
(IV-ii) a DSC profile substantially as shown in FIG. 9;
(IV-iii) a TGA profile substantially as shown in FIG. 9.

In some embodiments, Form 3B is characterized by all three of the features (IV-i)-(IV-iii). In some embodiments, Form 3B is characterized by at least one of features (IV-ii) and (IV-iii) and feature (IV-iv) an XRPD pattern having peaks at 2θ angles of 10.8°, 14.5°, 16.9°, 19.3°, 21.2°, 23.7°, 24.0° and 28.8°.

Form 3C

FIG. 10 shows an XRPD pattern of Form 3C of the Hydrochloride Salt obtained using CuKα radiation. Peaks identified in FIG. 10 include those listed in Table 5.

TABLE 5

| Angle 2θ° | Intensity % |
|---|---|
| 8.92 | 35.3 |
| 10.99 | 100.0 |
| 12.24 | 61.0 |
| 13.37 | 16.0 |
| 14.13 | 36.2 |
| 14.86 | 57.6 |
| 17.00 | 33.1 |
| 17.25 | 28.3 |
| 17.50 | 21.7 |
| 17.74 | 32.4 |
| 19.75 | 58.3 |
| 20.00 | 46.0 |
| 21.14 | 41.9 |
| 22.80 | 32.3 |
| 23.27 | 33.7 |
| 24.04 | 51.0 |
| 24.39 | 65.0 |
| 26.21 | 34.5 |
| 29.04 | 37.8 |

In some embodiments, Form 3C is characterized by an XRPD pattern having peaks at 2θ angles of 11.0°, 12.2° and 24.4°. In some embodiments, Form 3C is characterized by an XRPD pattern having peaks at 2θ angles of 11.0°, 12.2°, 14.9°, 19.8°, 24.0° and 24.4°. In some embodiments, Form 3C is characterized by an XRPD pattern having peaks at 2θ angles of 8.9°, 11.0°, 12.2°, 13.4°, 14.1°, 14.9°, 17.0°, 17.3°, 17.5°, 17.7°, 19.8°, 20.0°, 21.4°, 22.8°, 23.3°, 24.0°, 24.4°, 26.2° and 29.0°. In some embodiments, Form 3C is characterized by an XRPD pattern substantially as shown in FIG. 10.

FIG. 11 shows a DSC profile of Form 3C. The DSC graph plots the heat flow as a function of temperature from a sample, the temperature rate change being about 10° C./min. In some embodiments, Form 3C is characterized by a DSC profile characterized by an endothermic transition that has an onset temperature of 116.0° C., with a melt at 133.0° C. In some embodiments, Form 3C is characterized by a DSC profile substantially as shown in FIG. 11.

FIG. 11 also shows a TGA profile of Form 3C. The TGA profile plots the percent loss of weight of the sample as a function of temperature, the temperature rate change being about 10° C./min. The weight loss represents a loss of about 11.5% of the weight of the sample as the temperature is changed from 25° C. to 250° C. This corresponds to a loss of about 0.9 moles of methyl ethyl ketone, indicating Form 3C is a solvate. In some embodiments, Form 3C is characterized by a TGA profile substantially as shown in FIG. 11.

In some embodiments, Form 3C is characterized by at least two of the following features (V-i)-(V-iii):
 (V-i) an XRPD pattern having peaks at 2θ angles of 11.0°, 12.2° and 24.4°;
 (V-ii) a DSC profile substantially as shown in FIG. 11;
 (V-iii) a TGA profile substantially as shown in FIG. 11.

In some embodiments, Form 3C is characterized by all three features (V-i)-(V-iii). In some embodiments, Form 3C is characterized by at least one of features (V-ii) and (V-iii) and feature (V-iv) an XRPD pattern having peaks at 2θ angles of 11.0°, 12.2°, 14.9°, 19.8°, 24.0° and 24.4°.

Form 5

FIG. 12 shows an XRPD pattern of Form 5 of the Hydrochloride Salt obtained using CuKα radiation. Peaks identified in FIG. 12 include those listed in Table 6.

TABLE 6

| Angle 2θ° | Intensity % |
|---|---|
| 3.72 | 25.6 |
| 9.15 | 20.5 |
| 10.79 | 25.2 |
| 11.49 | 25.6 |
| 12.82 | 19.8 |
| 14.06 | 37.0 |
| 14.69 | 19.4 |
| 16.68 | 58.9 |
| 17.24 | 43.0 |
| 18.11 | 41.5 |
| 18.94 | 26.1 |
| 19.34 | 35.3 |
| 20.96 | 39.7 |
| 22.92 | 100 |
| 23.74 | 29.1 |
| 24.63 | 35.3 |
| 24.95 | 35.6 |
| 28.02 | 27.0 |

In some embodiments, Form 5 is characterized by an XRPD pattern having peaks at 2θ angles of 16.7° and 22.9°. In some embodiments, Form 5 is characterized by an XRPD pattern having peaks at 2θ angles of 16.7°, 17.2°, 18.1° and 22.9°. In some embodiments, Form 5 is characterized by an XRPD pattern having peaks at 2θ angles of 3.7°, 9.2°, 10.8°, 11.5°, 12.8°, 14.1°, 14.7°, 16.7°, 17.2°, 18.1°, 18.9°, 19.3°, 21.0°, 22.9°, 23.7°, 24.6°, 25.0° and 28.0°. In some embodiments, Form 5 is characterized by an XRPD pattern substantially as shown in FIG. 12.

FIG. 13 shows a DSC profile of Form 5 of the Hydrochloride Salt. The DSC profile plots the heat flow as a function of temperature from a sample, the temperature rate change being about 10° C./min. In some embodiments, Form 5 is characterized by a DSC profile characterized by two endothermic transitions, the first endothermic transition having an onset temperature of 64.1° C., with a melt at 82.3° C., and the second endothermic transition being broad and having an onset temperature of 116.8° C. In some embodiments, Form 5 is characterized by a DSC profile substantially as shown in FIG. 13.

FIG. 13 also shows a TGA profile of Form 5 of the Hydrochloride Salt. The TGA profile plots the percent loss of weight of the sample as a function of temperature, the temperature rate change being about 10° C./min. The weight loss represents a loss of about 18.3% of the weight of the sample as the temperature is changed from 25° C. to 250° C. This corresponds to a loss of about 1.5 moles of tetrahydrofuran, indicating Form 5 is a solvate. In some embodiments, Form 5 is characterized by a TGA profile substantially as shown in FIG. 13.

In some embodiments, Form 5 is characterized by at least two of the following features (VI-i)-(VI-iii):
 (VI-i) an XRPD pattern having peaks at 2θ angles of 16.7° and 22.9°.
 (VI-ii) a DSC profile substantially as shown in FIG. 13;
 (VI-iii) a TGA profile substantially as shown in FIG. 13.

In some embodiments, Form 5 is characterized by all three of the features (VI-i)-(VI-iii). In some embodiments, Form 5 is characterized by at least one of features (VI-ii) and (VI-iii) and feature (VI-iv) an XRPD pattern having peaks at 2θ angles of 16.7°, 17.2°, 18.1° and 22.9°.

Form 7

FIG. 14 shows an XRPD pattern of Form 7 of the Hydrochloride Salt obtained using CuKα radiation. Peaks identified in FIG. 14 include those in Table 7.

TABLE 7

| Angle 2θ° | Intensity % |
|---|---|
| 8.98 | 17.3 |
| 10.01 | 33.8 |
| 13.48 | 29.7 |
| 14.07 | 21.8 |
| 15.40 | 49.4 |
| 15.94 | 22.1 |
| 16.57 | 30.5 |
| 17.29 | 43.8 |
| 17.97 | 31.3 |
| 18.33 | 38.9 |
| 19.60 | 47.5 |
| 20.14 | 20.7 |
| 20.79 | 27.2 |
| 22.03 | 33.5 |
| 22.48 | 100 |
| 23.43 | 13.7 |
| 23.93 | 17.6 |
| 24.28 | 17.0 |
| 24.61 | 13.5 |
| 26.87 | 19.6 |
| 27.36 | 11.1 |
| 27.79 | 17.5 |
| 28.32 | 17.0 |

In some embodiments, Form 7 is characterized by an XRPD pattern having peaks at 2θ angles of 15.4°, 17.3°, 19.6° and 22.5°. In some embodiments, Form 7 is characterized by an XRPD pattern having peaks at 2θ angles of 10.0°, 15.4°, 16.6°, 17.3°, 18.0°, 18.3°, 19.6°, 22.0° and 22.5°. In some embodiments, Form 7 is characterized by an XRPD pattern having peaks at 2θ angles of 9.0°, 10.0°, 13.5°, 14.1°, 15.4°, 15.9°, 16.6°, 17.3°, 18.0°, 18.3°, 19.6°, 20.1°, 20.8°, 22.0°, 22.5°, 23.4°, 23.9°, 24.3°, 24.6°, 26.9°, 27.4°, 27.8° and 28.3°. In some embodiments, Form 7 is characterized by an XRPD pattern substantially as shown in FIG. 14.

FIG. 15 shows a DSC profile of Form 7 of the Hydrochloride Salt. The DSC profile plots the heat flow as a function of temperature from a sample, the temperature rate change being about 10° C./min. In some embodiments, Form 7 is characterized by a DSC profile characterized by a weak endothermic transition with an onset temperature of 65.5° C. and a melt at 86.8° C. In some embodiments, Form 7 is characterized by a DSC profile substantially as shown in FIG. 15.

FIG. 15 also shows a TGA profile of Form 7 of the Hydrochloride Salt. The TGA profile plots the percent loss of weight of the sample as a function of temperature; the temperature rate change being about 10° C./min. The weight loss represents a loss of about 23.6% of the weight of the sample as the temperature is changed from 25° C. to 250° C. This corresponds to a loss of about 1.7 moles of dioxane, indicating Form 7 is a solvate. In some embodiments, Form 7 is characterized by a TGA profile substantially as shown in FIG. 15.

In some embodiments, Form 7 is characterized by at least two of the following features (VII-i)-(VII-iii):
(VII-i) an XRPD pattern having peaks at 2θ angles of 15.4°, 17.3°, 19.6° and 22.5°;
(VII-ii) a DSC profile substantially as shown in FIG. 15;
(VII-iii) a TGA profile substantially as shown in FIG. 15.

In some embodiments, Form 7 is characterized by all of the features (VII-i)-(VII-iii). In some embodiments, Form 7 is characterized by at least one of features (VII-ii) and (VII-iii), and feature (VII-iv) an XRPD pattern having peaks at 2θ angles of 10.0°, 15.4°, 16.6°, 17.3°, 18.0°, 18.3°, 19.6°, 22.0° and 22.5°.

Some embodiments of the invention relate to a crystalline form wherein the crystalline form may be characterized by a combination of the characteristics described above for each crystalline form. In some embodiments, the crystalline form may be characterized by one or more of the following features (VIII-i)-(VIII-iv):
(VIII-i) a weight loss associated with a designated temperature range as determined from the TGA profile;
(VIII-ii) a temperature at which a particular weight loss transition begins as determined from the TGA profile;
(VIII-iii) a temperature associated with the maximum heat flow during a heat flow transition as determined from the DSC profile;
(VIII-iv) a temperature at which a sample begins to undergo a heat flow transition as determined from the DSC profile.

In some embodiments, the crystalline form is characterized by two or more of the features (VIII-i)-(VIII-iv). In some embodiments, the crystalline form is characterized by three or more of the features (VIII-i)-(VIII-iv). In some embodiments, the crystalline form is characterized by all four of the features (VIII-i)-(VIII-iv). In some embodiments, the crystalline form is characterized by one or more of the features (VIII-i)-(VIII-iv) and feature (VIII-v) the location of at least one of the major peaks in a corresponding XRPD pattern.

The combinations of characterizations that are discussed above may be used to describe any of the crystalline forms of the Hydrochloride Salt discussed herein (e.g., Form 1, 2, 3A, 3B, 3C, 5 or 7).

Some embodiments of the invention relate to a crystalline Hydrochloride Salt comprising a mixture of two or more of the different crystalline forms described above. In such embodiments, the crystalline Hydrochloride Salt is characterized by a combination of the aforementioned characteristics of each of the different crystalline forms it contains. The characterization is by any combination of one or more of the XRPD, TGA, and DSC characteristics, as described above for a particular crystalline form.

In some embodiments, Form 5 can be desolvated to give Form 1. In some embodiments, Form 5 can be desolvated to give Form 1 at a temperature of between about 70° C. and 100° C. In some embodiments, Form 5 can be desolvated to give a mixture of Form 1 and Form 5. In some embodiments, Form 5 can be desolvated to give a mixture of Form 1 and Form 5, by standing at ambient conditions for about 5 days.

In some embodiments, Form 7 can be desolvated to give Form 1. In some embodiments, Form 7 can be desolvated to give Form 1 at a temperature of between about 70° C. and 90° C. In some embodiments, Form 7 can be desolvated to give a mixture of Form 1 and Form 7. In some embodiments, Form 7 can be desolvated to give a mixture of Form 1 and Form 7 by standing at ambient conditions for about 3 days.

In some embodiments, Form 3A can be desolvated to give Form 1. In some embodiments, Form 3A can be desolvated to give a mixture of Form 1 and Form 3A.

In some embodiments, Form 3B can be desolvated to give Form 1. In some embodiments, Form 3B can be desolvated to give a mixture of Form 1 and Form 3B.

In some embodiments, Form 3C can be desolvated to give Form 1. In some embodiments, Form 3C can be desolvated to give a mixture of Form 1 and Form 3C.

Pharmaceutical Compositions and Methods

The compound of formula (I), or a crystalline form thereof, or a solvate thereof, is a useful inhibitor of E1 enzyme activity. In particular, the compound of formula (I), or a crystalline form thereof, or a solvate thereof, is useful as an inhibitor of NAE. An inhibitor is meant to include compounds which reduce the promoting effects of E1 enzymes in ubl conjugation to target proteins (e.g., reduction of ubiquitination, neddylation), reduce intracellular signaling mediated by ubl conjugation, and/or reduce proteolysis mediated by ubl conjugation (e.g., inhibition of cullin-dependent ubiquitination and proteolysis (e.g., the ubiquitin-proteasome pathway)). Thus, the compound of formula (I), or a crystalline form thereof, or a solvate thereof, may be assayed for its ability to inhibit the E1 enzyme in vitro or in vivo, or in cells or animal models according to methods provided in further detail herein, or methods known in the art. The compound of formula (I), or a crystalline form thereof, or a solvate thereof, may be assessed for its ability to bind or mediate E1 enzyme activity directly. Alternatively, the activity of the compound of formula (I), or a crystalline form thereof, or a solvate thereof, may be assessed through indirect cellular assays, or assays measuring downstream effects of E1 activation to assess inhibition of downstream effects of E1 inhibition (e.g., inhibition of cullin-dependent ubiquitination and proteolysis). For example, activity may be assessed by detection of ubl-conjugated substrates (e.g., ubl-conjugated E2s, neddylated cullins, ubiquitinated substrates); detection of downstream protein substrate stabilization (e.g., stabilization of p27, stabilization of IκB); detection of inhibition of UPP activity; detection of downstream effects of protein E1 inhibition and substrate stabilization (e.g., reporter assays, e.g., NFκB reporter assays, p27 reporter assays). Assays for assessing activities are known in the art.

One embodiment of this invention relates to a pharmaceutical composition comprising a compound of formula (I), or a crystalline form thereof, or a solvate thereof, and a pharmaceutically acceptable carrier or diluent. The pharmaceutical compositions of the invention preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include, but are not limited to, ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as, but not limited to, an oil, water, an alcohol, and combinations of these. Solubilizing agents such as cyclodextrins including beta-cyclodextrin sulfobutylether and hydroxypropyl beta-cyclodextrin may be included. Other excepients present in the formulation include citric acid or sodium citrate. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes; e.g., to mask taste, to affect the site of dissolution or absorption, or to prolong drug action. Coatings may be applied to a tablet or to granulated particles for use in a capsule.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). Preferably, the composition is formulated for administration to a patient having or at risk of developing or experiencing a recurrence of the relevant disorder being treated. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of compound or composition sufficient, upon single or multiple dose administration, to cause a detectable decrease in E1 enzyme activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of E1 enzyme inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

One embodiment of the invention relates to a method of inhibiting or decreasing E1 enzyme activity in a sample comprising contacting the sample with the compound of formula (I), or a crystalline form thereof, or a solvate thereof, or a composition comprising the compound of formula (I), or a crystalline form thereof, or a solvate thereof. The sample, as used herein, includes, without limitation, sample comprising purified or partially purified E1 enzyme, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of E1 enzyme activity in a sample may be carried out in vitro or in vivo, in cellulo, or in situ.

In another embodiment, the invention provides a method for treating a patient having a disorder, a symptom of a disorder, at risk of developing, or experiencing a recurrence of a disorder, comprising administering to the patient a pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Disease applications include those disorders in which inhibition of E1 enzyme activity is detrimental to survival and/or expansion of diseased cells or tissue (e.g., cells are sensitive to E1 inhibition; inhibition of E1 activity disrupts disease mechanisms; reduction of E1 activity stabilizes protein which are inhibitors of disease mechanisms; reduction of E1 activity results in inhibition of proteins which are activators of disease mechanisms). Disease applications are also intended to include any disorder, disease or condition which requires effective cullin and/or ubiquitination activity, which activity can be regulated by diminishing E1 enzyme activity (e.g., NAE activity).

For example, methods of the invention are useful in treatment of disorders involving cellular proliferation, including, but not limited to, disorders which require an effective cullin-dependent ubiquitination and proteolysis pathway (e.g., the ubiquitin proteasome pathway) for maintenance and/or progression of the disease state. The methods of the invention are useful in treatment of disorders mediated via proteins (e.g., NFκB activation, $p27^{Kip}$ activation, $p21^{WAF/CIP1}$ activation, p53 activation) which are regulated by E1 activity (e.g., NAE activity). Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease; Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compound of formula (I), or a crystalline form thereof, or a solvate thereof, and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

In some embodiments, the compound or composition of the invention is used to treat a patient having or at risk of developing or experiencing a recurrence in a cancer selected from the group consisting of colorectal cancer, ovarian cancer, lung cancer, breast cancer, gastric cancer, prostate cancer, and pancreatic cancer. In certain preferred embodiments, the cancer is selected from the group consisting of lung cancer, colorectal cancer, ovarian cancer and hematologic cancers.

Depending on the particular disorder or condition to be treated, in some embodiments, the E1 enzyme inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated". The other therapeutic agent may be administered prior to, at the same time as, or following administration of the E1 inhibitor of the invention.

In some embodiments, the compound of formula (I); or a crystalline form thereof, or a solvate thereof, or pharmaceutical compositions of the invention of the invention are administered in conjunction with a therapeutic agent selected from the group consisting of cytotoxic agents, radiotherapy, and immunotherapy appropriate for treatment of proliferative disorders and cancer. Non-limiting examples of cytotoxic agents suitable for use in combination with the E1 enzyme inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs including, e.g., CC-5013 and CC-4047; protein tyrosine kinase inhibitors, including, e.g., imatinib mesylate and gefitinib; proteasome inhibitors, including, e.g., bortezomib; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, Il-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

General Synthetic Methods

In some embodiments, the compound of formula (I) Form 1 is synthesized from the compound of formula (II), by treating an ethanolic solution of the compound of formula (II) with an HCl solution in either ethanol or diethyl ether. In some embodiments, the molarity of the HCl solution is about 0.9 M to about 1.3 M. In some embodiments, when using the ethanolic HCl solution, the ethanolic solution of the compound of formula (II) is heated to a temperature of about 45° C. to about 55° C. before the HCl solution is added. In some embodiments, when using the diethyl ether HCl solution, the ethanolic solution of the compound of formula (II) is stirred at a temperature of less than about 25° C. while the diethyl ether HCl solution is added.

Forms 2, 3A, 3B, 3C, 5 and 7 can be synthesized by treating the amorphous compound of formula (I) with the appropriate solvent. In some embodiments, the crystalline form is generated by maturation using heat/cool cycles of the amorphous compound of formula (I) with the appropriate solvent. In some embodiments, the crystalline form is generated by stirring the resulting slurry generated from the amorphous compound of formula (I) and the appropriate solvent, followed by evaporation of the excess solvent, or filtration of the crystalline material. In some embodiments, the crystalline form is generated by standing the resulting slurry generated from the amorphous compound of formula (I) and the appropriate solvent, at RT or in the freezer overnight, followed by evaporation of the excess solvent, or filtration of the crystalline material.

EXAMPLES

Abbreviations

DMF dimethylformamide
DSC differential scanning calorimetry
DMSO dimethylsulfoxide
EtOAc ethyl acetate
EtOH ethanol
MeOH methanol
MEK methyl ethyl ketone
THF tetrahydrofuran
HRMS high resolution mass spectrum
hr hours
min minutes
m/z mass to charge
MS mass spectrum
NMR nuclear magnetic resonance
RP LC-MS reverse phase liquid chromatography-mass spectrometry
RT room temperature
XRPD X-ray powder diffraction

General Methods

Proton nuclear magnetic resonance spectra are obtained on a Varian Mercury 300 spectrometer at 300 MHz.

X-Ray Powder Diffractometry (XRPD):

X-ray powder diffraction patterns for the samples are acquired on either:

Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection is Diffrac Plus XRD Commander v2.5.0, and the data are analysed and presented using Diffrac Plus EVA v 11.0.0.2 or v 13.0.0.2. Samples are run under ambient conditions. Approximately 30 mg of the sample is gently packed into a cavity cut into polished, zero-background (510) silicon wafer. The sample is covered by a Kapton film to prevent any contamination of the instrument during analysis. The film could also reduce evaporation of solvent contained in the material. The sample is rotated in its own plane during analysis. The data are collected at an angular range of 2 to 42° 2θ; with a step size of 0.05° 2θ; and a collection time of 0.5 s.step$^{-1}$.

Siemens D5000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976). The software used for data collection is Diffrac Plus XRD Commander v2.3.1 and the data are analyzed and presented using Diffrac Plus EVA v 11.0.0.2 or v 13.0.0.2. Samples are run under ambient conditions as flat plate specimens. Approximately 35 mg of the sample is gently packed into a cavity cut into polished, zero-background (510) silicon wafer. The sample is rotated in its own plane during analysis. The data are collected at an angular range of 2 to 42° 2θ; with a step size of 0.05° 2θ; and a collection time of 4 s.step$^{-1}$.

The XRPD may also be collected on a Bruker D8Advance. The data are collected over an angular range of 2.9° to 29.6° 2θ in continuous scan mode using a step size of 0.05° 2θ and a step time of 2 seconds. The sample is run under ambient conditions and prepared as a flat plate specimen using powder without grinding. The control software is Diffrac Plus XRD Commander v 2.3.1, and the analysis software is Diffrac Plus EVA v 9.0.0.2. The samples are run either static or rotated under ambient conditions.

Differential Scanning Calorimetry (DSC):

Differential scanning calorimetry (DSC) data are collected either on a Mettler DSC 823e equipped with a 50 position auto-sampler, or on a TA Instruments Q100 differential scanning calorimeter equipped with a 50 position auto-sampler, or on a TA Instruments Q200 differential scanning calorimeter. The energy and temperature calibration standard is indium. Samples are typically heated at a rate of 10° C. per minute between 25° C. and 250° or 300° C. A nitrogen purge flowing at 50 mL per minute is maintained over the sample during a scan. Between 0.5 mg and 3 mg of sample is analyzed. Samples are either crimped in a hermetically sealed aluminum pan with a pinhole to alleviate the pressure accumulated from the solvent vapor, or in a hermetically sealed aluminum pan without a pinhole.

Thermal Gravimetric Analysis (TGA):

Thermal gravimetric analysis (TGA) data are collected on either:

i) a Mettler TGA/SDTA 851e equipped with a 34 position autosampler, calibrated using certified indium. Typically 5-30 mg of each sample is loaded onto a pre-weighed aluminium crucible, and is heated at 10° C./min from ambient temperature to 250° C. A nitrogen purge flowing at 50 mL per minute is maintained over the sample;

ii) a TA Instruments Q500 thermal gravimetric analyzer, calibrated with Nickel/Alumel and running at a scan rate of 10° C. per minute. A nitrogen purge flowing at 60 mL per minute is maintained over the sample during measurements. Typically 10 mg to 15 mg of sample is loaded onto a pre-tared platinum crucible.

Example 1

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1

Step 1: Preparation of (1S,2S,4R)-4-{4-[(1S)-2,3-dihydro-1H-inden-1-ylamino]-7H-pyrrolo[2,3-d]pyrimidin-7-yl}-2-(hydroxymethyl)cyclopentanol A jacketed reactor was charged with (1S,2S,4R)-4-(4-chloro-7H-pyrrolo[2,3-d]pyrimidin-7-yl)-2-(hydroxymethyl)cyclopentanol (30.8 Kg, 115.05 mol), 2-butanol (198.5 Kg), (S)-(+)-1-aminoindane (16.95 Kg, 127.26 mol) and diisopropylethylamine (19.45 Kg, 150.50 mol). The mixture was heated to 55±5° C. and then moved to a mobile vessel. The reactor was then rinsed with 2-butanol (15.6 Kg) at 55±5° C. which was moved to the mobile vessel. The mobile vessel contents were then transferred to a pressure reactor and 2-butanol (51 L) was used to rinse the mobile vessel. The reaction mixture was then heated to 135±5° C. and adjusted to a pressure of 8 bar. The mixture was then stirred until reaction was complete by HPLC analysis. The mixture was cooled to 30±10° C. and transferred to a mobile vessel via a plate filter. The pressure reactor was rinsed with 2-butanol (43.1 L). The contents of the mobile vessel were then charged to a jacketed reactor via an in-line filter and the vessel rinsed with 2-butanol (39.2 Kg). The mixture was heated to 50±5° C. and concentrated under reduced pressure to about 50 L. The mixture was cooled to 20±5° C. and then dichloromethane (256 Kg) added over a period of about 3 hours. The mixture was stirred for a further 9.5 hours and then further cooled to 0±5° C. and stirred for about 4 hours. The solid product was isolated by filtration and washed with dichloromethane (82 Kg) at 0±5° C. The solids were then dried under reduced pressure at 40±5° C. to constant weight. A reactor was charged with water (371 Kg) and the dried solids and the mixture stirred at 20±5° C. for about 14.5 hours. The solid product was isolated by filtration and washed with water (371 Kg). The solids were then dried under reduced pressure at 50±5° C. to afford the title compound (32.4 Kg) as a white solid. $^1$H NMR (300 MHz, DMSO, 6): 8.15 (s, 1H), 7.71 (d, 1H), 7.07-7.29 (m, 5H), 6.61 (d, 1H), 5.88 (dd, 1H), 5.24-5.38 (m, 1H), 4.60 (d, 1H), 4.26-4.37 (m, 2H), 3.53-3.65 (m, 1H), 3.35-3.46 (m, 1H), 2.90-3.04 (m, 1H), 2.75-2.90 (m, 1H), 2.33-2.56 (m, 2H), 2.04-2.14 (m, 2H), 1.88-2.03 (m, 2H), 1.74-1.87 (m, 1H).

Step 2: Preparation of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (II)

A jacketed reactor was charged with (1S,2S,4R)-4-{4-[(1S)-2,3-dihydro-1H-inden-1-ylamino]-7H-pyrrolo[2,3-d]pyrimidin-7-yl}-2-(hydroxymethyl)cyclopentanol (15.1 Kg, 41.43 mol), acetonitrile (86.2 Kg) and Sulfamating Reagent, prepared as described below (36.7 Kg, 83.4 mol). The mixture was heated to 46±6° C. and stirred until reaction was complete by HPLC analysis. The mixture was cooled to 20±5° C. and a solution of 0.5N aqueous hydrochloric acid (83.95 Kg) added maintaining a temperature below 25° C. The mixture is stirred vigorously until by-product consumption was complete by HPLC analysis. The layers were then separated and the aqueous phase extracted with tert-butyl methyl ether (56.2 Kg). The organic phases were combined and further tert-butyl methyl ether (18.1 Kg) was added. The organic phase was then washed with water (151.3 L). Acetonitrile (119.3 Kg) was added and the mixture then concentrated under reduced pressure to about 190 L. Further acetonitrile (77.6 Kg) was added and the mixture again concentrated under reduced pressure to about 190 L. The mixture was then cooled to −2.5±2.5° C. and concentrated hydrochloric acid (53.0 Kg) was added slowly maintaining a temperature below 5° C. The mixture was then warmed to 15±5° C. and stirred until reaction (deprotection) was complete by HPLC analysis. Water (151.1 L) was added maintaining a temperature below 25° C. followed by portion wise addition of sodium bicarbonate (46.0 Kg). The mixture was then heated at 20±5° C. for 1.5 hours. Ethyl acetate (137.1 Kg) was added and the mixture stirred for 1 hour. The layers were separated and the organic phase washed with water (150.7 L). The organic phase was then washed with 5% aqueous sodium chloride solution (2×159 Kg). The mixture was then concentrated under reduced pressure to about 100 L. A bed of acid washed activated charcoal (11.1 Kg) was equilibrated with ethyl acetate (48.3 Kg). The organic mixture was then passed through the charcoal bed (utilizing vacuum and pressure) and subsequent in-line filters (to remove any charcoal). The charcoal bed was then washed with ethyl acetate (245.2 Kg). The mixture was then concentrated to about 40 L under reduced pressure maintaining a temperature below 40° C. Ethyl acetate (87.7 Kg) was added and the mixture concentrated to about 40 L under reduced pressure maintaining a temperature below 40° C. Ethyl acetate (91.3 Kg) was added and the mixture concentrated to about 40 L under reduced pressure maintaining a temperature below 40° C. Ethyl acetate (88.6 Kg) was added and the mixture concentrated to about 40 L under reduced pressure maintaining a temperature below 40° C. Ethyl acetate (94.7 Kg) was added and the mixture concentrated to about 40 L under reduced pressure maintaining a temperature below 40° C. The mixture was then heated to 50±5° C. and dichloromethane (89.7 Kg) added at a rate to maintain a temperature of 50±5° C. The mixture was then seeded with the title compound (55 g) and further dichloromethane (502.6 Kg) added over 4 hours maintaining a temperature of 45±5° C. After stirring for a further 30 minutes the mixture was cooled to 20±5° C. and stirred for 16 hours. The mixture was then cooled to 2.5±2.5° C. and stirred for 8 hours. The solid product was isolated by filtration and washed with dichloromethane (1×50.1 Kg and 1×49.8 Kg) at 2.5±2.5° C. The solids were then dried under reduced pressure at ≤35° C. to afford the title compound (6.1 Kg) as a white solid. $^1$H NMR (300 MHz, DMSO, 8): 8.15 (s, 1H), 7.73 (d, 1H), 7.40 (s, 2H), 7.06-7.29 (m, 5H), 6.61 (d, 1H), 5.88 (dd, 1H), 5.26-5.42 (m, 1H), 4.90 (d, 1H), 4.26-4.35 (m, 1H), 4.14-4.25 (m, 1H), 3.95-4.07 (m, 1H), 2.90-3.04 (m, 1H), 2.75-2.89 (m, 1H), 2.62-2.74 (m, 1H), 2.40-2.55 (m, 1H), 1.97-2.18 (m, 3H), 1.83-1.96 (m, 2H).

Preparation of Sulfamating Reagent

Chlorosulfonyl isocyanate (45.2 Kg, 319.4 mol) was added to toluene (194.2 Kg) and the resulting solution cooled to between about 0-6° C. A solution of tert-butyl alcohol (23.6 Kg, 318.4 mol) in toluene (48.0 Kg) was then added over a period of 90 minutes, maintaining a temperature of between about 0-6° C. The mixture was then stirred until consumption of tert-butyl alcohol was complete (approximately 80 minutes). A solution of triethylenediamine (DABCO, 71.4 Kg, 636.5 mol) in toluene (293.0 Kg) was then added to the mixture over a period of 2.5 hours, maintaining a temperature of between about 0-6° C. The mixture was then warmed to 20-25° C. and stirred for 8 hours. The solid product was isolated by centrifugal filtration under a nitrogen atmosphere and washed with toluene (180.8 Kg) and then tert butyl methyl ether (51.0 gallons) and spun until no further liquors were seen to be expelled (approximately 60 minutes). The solids were then further dried under vacuum to afford 132.9 Kg of the Sulfamating Reagent.

Step 3: Synthesis of ((1S,2S,4R)-4-[4-{(1S)-2,3-dihydro-1H-inden-1-ylamino]-7H-pyrrolo[2,3-d]pyrimidin-7-yl}-2-hydroxycyclopentyl)methyl sulfamate hydrochloride Form 1

A reactor was charged with ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (13.4 Kg, 30.2 mol) and 200-proof ethanol (106.2 Kg). The mixture was heated to reflux to afford a clear solution. The mixture was cooled to 50±5° C. and passed through a cartridge filter. 200 proof ethanol (8.9 Kg) was used to rinse the filter. 1.27M hydrogen chloride in ethanol (10.2 Kg) was added via a cartridge filter at a rate to maintain a temperature of 50±5° C. The mixture was then seeded with Form 1 (67 g). Further 1.27M HCl (10.2 Kg) was added via a cartridge filter at a rate to maintain a temperature of 50±5° C. The mixture was then stirred at 50±5° C. for about 3 hours. The mixture was then cooled to 20±5° C. over about 3 hours and then stirred for about 2.5 hours. The solid product was then isolated by filtration and washed with 200-proof ethanol (1×20.4 Kg and 1×21.2 Kg). The solids were dried by aspiration on the filter until no supernatant was seen to be collected, and then further dried under reduced pressure at ≤30° C. to afford the title compound (12.2 Kg) as a white solid determined to be Form 1 by XRPD. $^1$H NMR (300 MHz, DMSO, δ): 9.83 (s, 1H), 8.34 (s, 1H), 7.62 (s, 1H), 7.44 (s, 2H), 7.30 (m, 3H), 7.22 (t, 1H), 7.07 (s, 1H), 5.86 (dd, 1H), 5.42 (m, 1H), 4.32 (m, 1H), 4.21 (dd, 1H), 4.02 (dd, 1H), 3.04 (m, 1H), 2.88 (m, 1H), 2.67 (m, 2H), 2.15 (m, 2H), 2.08 (m, 2H), 1.94 (m, 1H). XRPD data for Form 1 is shown in FIG. 1 and Table 1; DSC data is shown in FIG. 2, and TGA data for Form 1 is shown in FIG. 3.

Alternative Preparation of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1

To a reaction vessel is added ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (1 equiv.) and ethanol (15 volumes with respect to input material) and the mixture is stirred at 20-25° C. 1.0M hydrogen chloride in ethanol (1 equiv. with respect to input material) is added at a rate as to maintain temperature at ≤25° C. The mixture is then stirred at 20±5° C. for a minimum of 4 hours. The solid product is isolated by filtration and washed with ethanol (2×2.5 volumes with respect to input material). The product is then dried by aspiration on the filter and then under reduced pressure at a temperature of 30±5° C. to give the title compound.

Alternative Preparation of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1

A flask was charged with ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (25 g, 56.4 mmol) and 200-proof ethanol (300 mL). The mixture was heated to 70-75° C. to afford a clear solution. The mixture was cooled to 50±5° C. 1.25M hydrogen chloride in ethanol (25 mL, 31 mmol) was added rapidly at a rate to maintain a temperature of 50±5° C. The mixture was then seeded with Form 1. Further 1.25M HCl (25 mL, 31 mmol) was added over a period of about 60 minutes, maintaining a temperature of 50±5° C. The mixture was then stirred at 50±5° C. for about 2 hours. The mixture was then cooled to 20±5° C. over about 2 hours and then stirred for about 17 hours. The solid product was then isolated by filtration and washed with 200-proof ethanol (50 mL). The solids were dried by aspiration on the filter for about 5 hours, and then further dried under reduced pressure at 30-35° C. to afford the title compound (22.5 g) as a white solid.

Example 2

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate Form 2

8 volumes of H$_2$O were added to amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (100 mg), which was matured using 4 hour heat/cool cycles (RT to 40° C.) for 3 days with shaking. The resulting solid was filtered under vacuum without further drying. XRPD data for Form 2 is shown in FIG. 4 and Table 2; DSC and TGA data for Form 2 are both shown in FIG. 5.

Example 3

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3A 8 volumes of EtOH were added to amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (44 mg) in a 4 mL vial After standing in the fridge for 30 minutes the resulting slurry was placed on a glass slide and the excess solvent was allowed to evaporate to give Form 3A. Form 3A was analyzed by XRPD, DSC and TGA. XRPD data for Form 3A is shown in FIG. 6 and Table 3; DSC and TGA data are both shown in FIG. 7.

Example 4

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3B 20 volumes of EtOAc were added to amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (120 mg) in a vial and stirred at 10° C. overnight, then kept in the freezer. The excess solvent was evaporated from the slurry and the resulting crystalline material Form 3B was analyzed by XRPD, DSC and TGA. XRPD data for Form 3B is shown in FIG. 8 and Table 4; DSC and TGA data are both shown in FIG. 9.

Example 5

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3C 12 volumes of MEK were added to amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (110 mg) in a 4 mL vial and stirred at RT overnight, then kept in the freezer at –20° C. The slurry was then filtered and the resulting crystalline material Form 3C was analyzed by XRPD, DSC and TGA. XRPD data for Form 3C is shown in FIG. 10 and Table 5; DSC and TGA data are both shown in FIG. 11.

Example 6

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloridie Form 5

3 volumes of THF were added to amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (192 mg) in a 4 mL vial. The resulting slurry was stirred at RT overnight. An additional 3 volumes of THF were added and the slurry was then kept in the freezer at −20° C. The slurry was filtered and the resulting crystalline material was analyzed without further drying. XRPD data for Form 5 is shown in FIG. 12 and Table 6; DSC and TGA data are both shown in FIG. 13.

Example 7

Synthesis of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 7

10 volumes of dioxane were added to amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (68 mg) in a 4 mL vial, and was stirred at RT overnight, and then in the freezer. The slurry was placed on the sample holder and the excess solvent was allowed to evaporate and was then analyzed by XRPD. XRPD data for Form 7 is shown in FIG. 14 and Table 7; DSC and TGA data are both shown in FIG. 15.

Example 8

Synthesis of Amorphous ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride (1.14 g) was dissolved in 70% w/w tert-butyl alcohol/H$_2$O (70 times by weight) to give a clear solution which was filtered through an 0.45 micron filter. The solution was then frozen using a dry ice/acetone mixture and freeze-dried overnight to yield the title compound.

Example 9

Preparation of Formulation of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1

Citric acid and sulfobutylether-beta-cyclodextrin (Captisol®, CyDex, Lenexa, Kans.) are dissolved in water for injection. Once a solution is obtained, ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1 (Hydrochloride Salt Form 1) is added and dissolved. The pH is adjusted to 3.3±0.2 with 2N Sodium Hydroxide. The mixture is filtered; first through a clarifying filter (0.45 µM), then through a sterilizing filter (0.2 µM). The mixture is then aspectically filled into vials using an automated system, followed by capping with Flip-Off® caps with aluminum seals. The composition of the formulation is shown in Table 8 below.

TABLE 8

|  | Concentration | Amount per Unit Dosage Form |
| --- | --- | --- |
| Hydrochloride Salt Form 1 | 10 mg/mL (calculated as free base) | 50 mg |
| Citric Acid | 9.6 mg/mL | 48 mg |

TABLE 8-continued

|  | Concentration | Amount per Unit Dosage Form |
| --- | --- | --- |
| Sulfobutylether-beta-cyclodextrin | 100 mg/mL | 500 mg |
| Sodium Hydroxide |  | To pH 3.3 |
| Water for Injection |  | 5 mL |

Example 10

The following table summarizes stability data obtained (Peak Area % measured by HPLC) for solid state ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate.

TABLE 9

|  |  | Peak Area % | | |
| --- | --- | --- | --- | --- |
|  | Storage Conditions | Initial | 15 days | 6 weeks |
| HCl Salt Form 1 | −20° C. freezer | 99.2 |  |  |
|  | 5° C. refrigerator |  |  | 99.3 |
|  | 40° C./75% RH† |  |  | 98.7 |
|  | 60° C./75% RH |  |  | 91.3 |
| HCl Salt Form 2 | −20° C. freezer | 98.3 |  |  |
|  | 5° C. refrigerator |  | 98.2 |  |
|  | 40° C./75% RH |  | 97.8 |  |
|  | 60° C./75% RH |  | 88.6 |  |
| potassium salt (amorphous) | −20° C. freezer | 96.9 |  |  |
|  | 5° C. refrigerator |  | 97.6 |  |
|  | 40° C./75% RH |  | 88.7 |  |
|  | 60° C./75% RH |  | 38.3 |  |
| free base (amorphous) | −20° C. freezer | 96.0 |  |  |
|  | 5° C. refrigerator |  | 96.4 |  |
|  | 40° C./75% RH |  | 94.5 |  |
|  | 60° C./75% RH |  | 93.2 |  |

†relative humidity

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A pharmaceutical composition comprising at least one crystalline form chosen from crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1, Form 2, Form 3A, Form 3B, Form 3C, Form 5, and Form 7 and a pharmaceutically acceptable carrier or diluent.

2. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 1.

3. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 2.

4. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3A.

5. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3B.

6. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 3C.

7. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 5.

8. Crystalline ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate hydrochloride Form 7.

9. The compound of claim 2, wherein Form 1 is characterized by an XRPD pattern having peaks at 2θ angles of 9.6°, 13.6° and 19.1°, wherein each 2θ angle value is ±0.2°.

10. The compound of claim 2, wherein Form 1 is characterized by an XRPD pattern having peaks at 2θ angles of 9.6°, 13.6°, 14.5°, 19.1° and 23.7°, wherein each 2θ angle value is ±0.2°.

11. The compound of claim 2, wherein Form 1 is characterized by at least two of (I-i)-(I-iv):
(I-i) an XRPD pattern having peaks at 2θ angles of 9.6°, 13.6° and 19.1°, wherein each 2θ angle value is ±0.2°;
(I-ii) a DSC profile as shown in FIG. 2;
(I-iii) a TGA profile as shown in FIG. 3; or
(I-iv) a solubility of about 7.8 mg/mL in water.

12. The compound of claim 3, wherein Form 2 is characterized by an XRPD pattern having peaks at 2θ angles of 8.7°, 18.2° and 23.8°, wherein each 2θ angle value is ±0.2°.

13. The compound of claim 3, wherein Form 2 is characterized by an XRPD pattern having peaks at 2θ angles of 8.7°, 18.2°, 19.4°, 23.8°, 24.3° and 27.5°, wherein each 2θ angle value is ±0.2°.

14. The compound of claim 3, wherein Form 2 is characterized by at least two of (II-i)-(II-iii):
(II-i) an XRPD pattern having peaks at 2θ angles of 8.7°, 18.2°, and 23.8°, wherein each 2θ angle value is ±0.2°;
(II-ii) a DSC profile as shown in FIG. 5; or
(II-iii) a TGA profile as shown in FIG. 5.

15. The compound of claim 4, wherein Form 3A is characterized by an XRPD pattern having peaks at 2θ angles of 10.9°, 14.6°, 19.5° and 24.0°, wherein each 2θ angle value is ±0.2°.

16. The compound of claim 4, wherein Form 3A is characterized by an XRPD pattern having peaks at 2θ angles of 10.9°, 14.6°, 19.5° and 24.0°, wherein each 2θ angle value is ±0.2°.

17. The compound of claim 4, wherein Form 3A is characterized by at least two of (III-i)-(III-iii):
(III-i) an XRPD pattern having peaks at b 2θ angles of 10.9°, 14.6°, 19.5° and 24.0°, wherein each 2θ angle value is ±0.2°;
(III-ii) a DSC profile as shown in FIG. 7; or
(III-iii) a TGA profile as shown in FIG. 7.

18. The compound of claim 5, wherein Form 3B is characterized by an XRPD pattern having peaks at 2θ angles of 10.8°, 16.9°, 23.7° and 24.0°, wherein each 2θ angle value is ±0.2°.

19. The compound of claim 5, wherein Form 3B is characterized by an XRPD pattern having peaks at 2θ angles of 10.8°, 14.5°, 16.9°, 19.3°, 21.2°, 23.7°, 24.0° and 28.8°, wherein each 2θ angle value is ±0.2°.

20. The compound of claim 5, wherein Form 3B is characterized by at least two of (IV-i)-(IV-iii):
(IV-i) an XRPD pattern having peaks at 2θ angles of 10.8°, 16.9°, 23.7° and 24.0°, wherein each 2θ angle value is ±0.2°;
(IV-ii) a DSC profile as shown in FIG. 9; or
(IV-iii) a TGA profile as shown in FIG. 9.

21. The compound of claim 6, wherein Form 3C is characterized by an XRPD pattern having peaks at 2θ angles of 11.0°, 12.2° and 24.4°, wherein each 2θ angle value is ±0.2°.

22. The compound of claim 6, wherein Form 3C is characterized by an XRPD pattern having peaks at 2θ angles of 11.0°, 12.2°, 14.9°, 19.8°, 24.0° and 24.4°, wherein each 2θ angle value is ±0.2°.

23. The compound of claim 6, wherein Form 3C is characterized by at least two of (V-i)-(V-iii):
(V-i) an XRPD pattern having peaks at 2θ angles of 11.0°, 12.2° and 24.4°, wherein each 2θ angle value is ±0.2°;
(V-ii) a DSC profile as shown in FIG. 11; or
(V-iii) a TGA profile as shown in FIG. 11.

24. The compound of claim 7, wherein Form 5 is characterized by an XRPD pattern having peaks at 2θ angles of 16.7° and 22.9°, wherein each 2θ angle value is ±0.2°.

25. The compound of claim 7, wherein Form 5 is characterized by an XRPD pattern having peaks at 2θ angles of 16.7°, 17.2°, 18.1° and 22.9°, wherein each 2θ angle value is ±0.2°.

26. The compound of claim 7, wherein Form 5 is characterized by at least two of (VI-i)-(VI-iv):
(VI-i) an XRPD pattern having peaks at 2θ angles of 16.7° and 22.9°, wherein each 2θ angle value is ±0.2°.
(VI-ii) a DSC profile as shown in FIG. 13; or
(VI-iii) a TGA profile as shown in FIG. 13.

27. The compound of claim 8, wherein Form 7 is characterized by an XRPD pattern having peaks at 2θ angles of 15.4°, 17.3°, 19.6° and 22.5°, wherein each 2θ angle value is ±0.2°.

28. The compound of claim 8, wherein Form 7 is characterized by an XRPD pattern having peaks at 2θ angles of 10.0°, 15.4°, 16.6°, 17.3°, 18.0°, 18.3°, 19.6°, 22.0° and 22.5°, wherein each 2θ angle value is ±0.2°.

29. The compound of claim 8, wherein Form 7 is characterized by at least two of (VII-i)-(VII-iii):
(VII-i) an XRPD pattern having peaks at 2θ angles of 15.4°, 17.3°, 19.6° and 22.5°, wherein each 2θ angle value is ±0.2°;
(VII-ii) a DSC profile as shown in FIG. 15; or
(VII-iii) a TGA profile as shown in FIG. 15.

* * * * *

UNITED STATES PATENT AND TRADEMARK OFFICE
CERTIFICATE OF CORRECTION

PATENT NO. : 9,187,482 B2
APPLICATION NO. : 12/779331
DATED : November 17, 2015
INVENTOR(S) : Ian G. Armitage et al.

It is certified that error appears in the above-identified patent and that said Letters Patent is hereby corrected as shown below:

On the title page, item 75, line 2, "Milton Road (GB)" should read -- Cambridge (GB) --.

In the claims

Claim 16, col. 33, lines 53-54, "angles of 10.9°, 14.6°, 19.5°, and 24.0°," should read -- angles of 10.9°, 14.6°, 16.9°, 19.5°, 24.0°, and 25.9°, --.

Claim 17, col. 33, line 58, "having peaks at b 2θ angles" should read -- having peaks at 2θ angles --.

Signed and Sealed this
Seventeenth Day of May, 2016

Michelle K. Lee
*Director of the United States Patent and Trademark Office*